(12) United States Patent
Bedalov et al.

(10) Patent No.: US 7,514,406 B2
(45) Date of Patent: Apr. 7, 2009

(54) METHODS FOR INHIBITING DEACETYLASE ACTIVITY

(75) Inventors: Antonio Bedalov, Seattle, WA (US);
Daniel E. Gottschling, Seattle, WA (US); Julian Simon, Seattle, WA (US)

(73) Assignee: Fred Hutchinson Cancer Research Center, Seattle, WA (US)

( * ) Notice: Subject to any disclaimer, the term of this patent is extended or adjusted under 35 U.S.C. 154(b) by 427 days.

(21) Appl. No.: 10/496,031

(22) PCT Filed: Nov. 26, 2002

(86) PCT No.: PCT/US02/38434
§ 371 (c)(1), (2), (4) Date: May 18, 2004

(87) PCT Pub. No.: WO03/046207
PCT Pub. Date: Jun. 5, 2003

(65) Prior Publication Data
US 2005/0079995 A1   Apr. 14, 2005

Related U.S. Application Data

(60) Provisional application No. 60/333,884, filed on Nov. 27, 2001.

(51) Int. Cl.
*A61K 38/00* (2006.01)
*A61K 31/50* (2006.01)

(52) U.S. Cl. ......................... 514/12; 514/247
(58) Field of Classification Search .................. 514/12, 514/247
See application file for complete search history.

(56) References Cited

U.S. PATENT DOCUMENTS

| | | | |
|---|---|---|---|
| 5,239,083 A | 8/1993 | Kumazawa et al. |
| 5,968,903 A | 10/1999 | Kaneko et al. |
| 5,989,897 A | 11/1999 | Pillus et al. |
| 6,200,989 B1 | 3/2001 | De Cillis et al. |
| 6,228,583 B1 | 5/2001 | Guarente et al. |
| 6,495,556 B2 | 12/2002 | Uckun et al. |
| 6,552,027 B2 | 4/2003 | Uckun et al. |
| 6,962,920 B2 | 11/2005 | Gangjee |
| 6,987,091 B2 | 1/2006 | Schramm et al. |
| 2003/0124101 A1 | 7/2003 | Gu et al. |
| 2003/0207325 A1 | 11/2003 | Guarente et al. |
| 2004/0005574 A1 | 1/2004 | Guarente et al. |

FOREIGN PATENT DOCUMENTS

| | | |
|---|---|---|
| JP | 2004-137157 | 5/2004 |
| WO | WO 00/10981 A1 | 3/2000 |
| WO | WO 0112189 A1 * | 2/2001 |
| WO | WO 03/004621 A2 | 1/2003 |
| WO | WO 03/046207 A2 | 6/2003 |
| WO | WO 2005/016342 A1 | 2/2005 |
| WO | WO 2005/113568 A1 | 12/2005 |
| WO | WO 2006/081329 A2 | 8/2006 |

OTHER PUBLICATIONS

Grozinger et al. (Journal of Biological Chemistry, vol. 276, No. 42, pp. 38837-38843, Oct. 2001).*
Vaziri et al. (Cell 2001; 107: 149-159).*
Bedalov et al. (PNAS 2001; 98: 15113-15118).*
Gura (Science, v278, 1997, pp. 1041-1042).*
Freshney (Culture of Animal Cells, A Manual of Basic Technique, Alan R. Liss, Inc., 1983, New York, p. 4).*
Dermer (Bio/Technology, 1994, 12:320).*
Gendy, Z., et al., "Synthesis of heterobicyclic nitrogen systems bearing the 1,2,4-triazine moiety as anti-HIV and anticancer drugs, part III," Department of Chemistry, Faculty of Education, Ain Shams University, Roxy, Cairo, Egypt, 2001, Pharmazie vol. 56, No. 5, pp. 376-383.
Grozinger, Christina M. et al, "Identification of a Class of Small Molecule Inhibitors of the Sirtuin Family of NAD-dependent Deacetylases by Phenotypic Screening," The Journal of Biological Chemistry, 2001, vol. 276., No. 42, pp. 38837-38843.
Ford, Jack et al., "Cancer-Specific Functions of SIRT1 Enable Human Epithelial Cancer Cell Growth and Survival," *Cancer Res 2005*; 65: (22), 10457-10463 (Nov. 15, 2005).
Heltweg, Birgit et al., "Antitumor Activity of a Small-Molecule Inhibitor of Human Silent Information Regulator 2 Enzymes," *Cancer Res 2006*; 66: (8), 4368-4377 (Apr. 15, 2006).
Ouaissi, Mehdi et al., "Histone Deacetylase Enzymes as Potential Drug Targets in Cancer and Parasitic Diseases," *Journal of Biomedicine and Biotechnology*; vol. 2006, Article ID 13474, 1-10 (2006).

* cited by examiner

*Primary Examiner*—Brandon J Fetterolf
(74) *Attorney, Agent, or Firm*—Townsend and Townsend and Crew LLP

(57) ABSTRACT

A method for identifying a compound that inhibits the $NAD^+$-dependent deacetylase activity of a SIR2 protein is disclosed. These compounds are useful for the treatment of cancers and other diseases, through the activation of silenced genes, through the promotion of apoptosis in cancerous cells, and through the inhibition of transcriptional repressor activity in oncogenes.

10 Claims, 6 Drawing Sheets

| Compound | Structure | Activity[a] | Compound | Structure | Activity[a] |
|---|---|---|---|---|---|
| S1 | 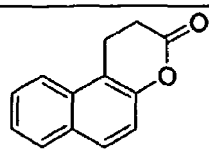 | + | S1h | 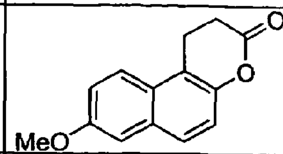 | + |
| S1a | 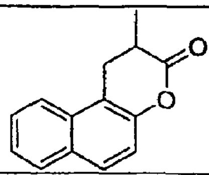 | + | S1i | 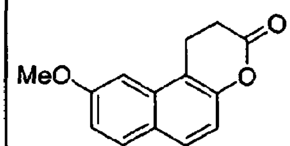 | ++ |
| S1b | 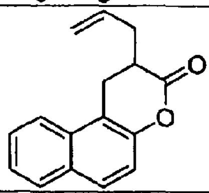 | ++ | S1j | 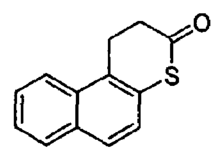 | ++ |
| S1c | 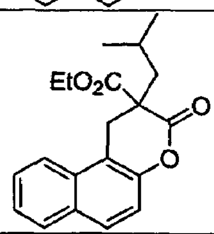 | ++ | S1k | 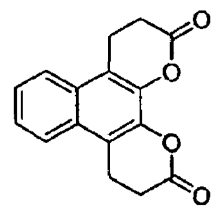 | ++ |
| S1d | 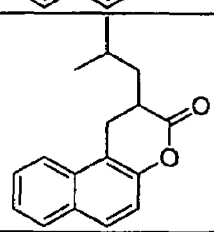 | ++ | S1l | 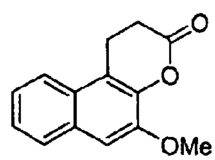 | + |
| S1e | 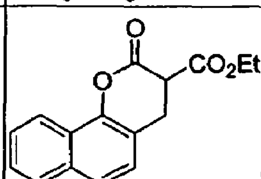 | + | S1m | 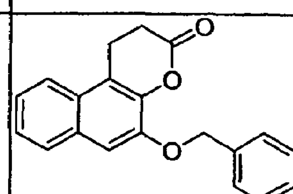 | +++ |
| S1f | 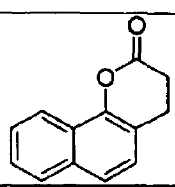 | ++ | S1n | 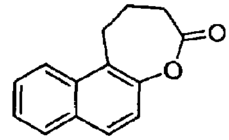 | +++ |
| S1g | 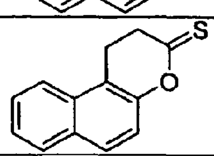 | +++ | | | |

[a] "+": IC$_{50}$ greater than 50 μM; "++": IC$_{50}$ less than 50 μM but greater than 20 μM; "+++": IC$_{50}$ less than 20 μM.

METHODS FOR INHIBITING DEACETYLASE ACTIVITY

CROSS-REFERENCES TO RELATED APPLICATIONS

This application claims the benefit of U.S. Provisional Application No. 60/333,884, filed Nov. 27, 2001. The foregoing application is hereby incorporated by reference in its entirety for all purposes.

REFERENCE TO A "SEQUENCE LISTING," A TABLE, OR A COMPUTER PROGRAM LISTING APPENDIX SUBMITTED ON A COMPACT DISK.

NOT APPLICABLE

STATEMENT AS TO RIGHTS TO INVENTIONS MADE UNDER FEDERALLY SPONSORED RESEARCH OR DEVELOPMENT

A portion of the present invention was made under federally sponsored research and development under National Heart, Lung, and Blood Institute Grant HL04211, National Institutes of Health Grant GM43893, and National Cancer Institute Grant CA78746. The Government may have rights in certain aspects of this invention.

BACKGROUND OF THE INVENTION

Portions of the eukaryotic genome can be maintained in a transcriptionally inactive, or silenced, state as the result of the local chromatin structure. Silent chromatin may encompass regions ranging from a few thousand base pairs, as in the silent mating type genes of the yeast S. cerevisiae (Loo, S. & Rine, J. (1995) Annu. Rev. Cell Dev. Biol. 11, 519-48), to whole chromosomes, such as the inactive X-chromosome in mammals (Lyon, M. F. (1999) Curr. Biol. 9, R235-7). The formation of silent chromatin, which is best understood at the S. cerevisiae silent mating type loci HMR and HML, and telomeres, depends on DNA elements, or silencers. The HM silencers are located in proximity to the genes they regulate and contain a combination of binding sites for Rap1p, Abf1p and the origin recognition complex (ORC) (Loo, S. & Rine, J. (1995) Annu. Rev. Cell Dev. Biol. 11, 519-48). These proteins recruit the SIR (Silent Information Regulator) protein complex (Sir2p-4p) through protein-protein interactions. Once recruited to silencers, the SIR complex is thought to spread along the chromatin through binding of Sir3p and Sir4p to the $NH_2$-terminal tails of histone H3 and H4 (reviewed in Gartenberg, M. R. (2000) Curr. Opin. Microbiol. 3, 132-7). Among the many requirements for silent chromatin (reviewed in Wu, J. & Grunstein, M. (2000) Trends Biochem. Sci. 25, 619-23), post-translational modification (i.e. acetylation, phosphorylation, methylation and ubiquitination) of the $NH_2$-terminal tails of histones appears to be critical. For example, the tails of histones H3 and H4 are hypoacetylated in silent chromatin compared to other regions of the genome (Braunstein, M. et al. (1993) Genes Dev. 7, 592-604). Of the SIR proteins, Sir2p has been shown to be an $NAD^+$-dependent histone deacetylase, and is responsible for the hypoacetylated state of histones in silent chromatin (Moazed, D. (2001) Curr. Opin. Cell Biol. 13, 232-8; Imai, S. et al. (2000) Nature 403, 795-800; Smith, J. S. et al. (2000) Proc. Natl. Acad. Sci. USA 97, 6658-63; Landry, J. et al. (2000) Proc. Natl. Acad. Sci. USA 97, 5807-11). Sir2p also acts at the ribosomal RNA gene cluster (rDNA) in the RENT protein complex, which does not include Sir3p or Sir4p (Straight, A. F. et al. (1999) Cell 97, 245-56), where it acts to repress recombination.

The yeast SIR2 gene is the defining member of a broadly conserved family of $NAD^+$-dependent deacetylases, termed sirtuins, found in organisms ranging from bacteria to humans (Frye, R. A. (2000) Biochem. Biophys. Res. Commun. 273, 793-8). Sirtuins are highly conserved and contain a conserved catalytic domain of approximately 275 amino acids (Grozinger, C. M. et al., (2001) J. Biol. Chem. 276, 38837-38843). In S. cerevisiae alone, four additional homologues have been identified, while in humans, eight homologues have been identified (Grozinger, C. M. et al. (2001) supra). The yeast SIR2 gene shares the greatest similarity with genes found in other eukaryotes, where it is believed that these closely related homologues serve a comparable role in silencing. Interestingly, SIR2 and its homologues have been implicated in the genetic regulation of aging, both in yeast and C. elegans (Tissenbaum, H. A. & Guarente, L. (2001) Nature 410, 227-30; Sinclair, D. A. & Guarente, L. (1997) Cell 91, 1033-42) and in metazoan development though the details of how it affects these fundamental processes are still mysterious.

Recently, several groups (Luo, J. et al. (2001) Cell 107, 137-48; and Vaziri, H. et al. (2001) Cell 107, 149-59) have explored the influence of the mammalian homologues, Sir2α (the mouse homologue of S. cerevisiae SIR2, also known as mSIRT1) and SIR2α (the human homologue of S. cerevisiae SIR2, also known as hSIRT1), on the activity of the p53 tumor suppressor gene. These studies indicate that deacetylase activity of Sir2α and SIR2α act on p53, resulting in suppression of the tumor suppressor activity. They have also shown that this deacetylase activity is dependent on nicotinamide adenosine dinucleotide (NAD).

What is needed in the art, is a method for inhibiting the $NAD^+$-dependent deacetylase activity of a member of the SIR2 family of proteins using a small molecule. Surprisingly, the present invention meets this need.

BRIEF SUMMARY OF THE INVENTION

In one aspect, the present invention provides a method for identifying compounds useful for the treatment of cancer or genetic blood diseases, comprising the step of determining whether the compound inhibits the deacetylase activity of a $NAD^+$-dependent deacetylase. In a related aspect of the present invention, the method for treating cancer or genetic blood diseases comprises the step of administering to a subject in need thereof, a therapeutically effective amount of a compound that inhibits the deacetylase activity of a $NAD^+$-dependent deacetylase.

In a second aspect of the present invention, a method is provided for identifying compounds which will be useful for the treatment of cancer or genetic blood diseases, comprising the step of determining whether the compound inhibits the $NAD^+$-dependent deacetylase activity of a member of the SIR2 family of proteins. In a related aspect of the present invention, the method for treating cancer or genetic blood diseases comprises the step of administering to a subject in thereof, a therapeutically effective amount of a compound that inhibits the $NAD^+$-dependent deacetylase activity of a member of the SIR2 family of proteins.

In a third aspect of the present invention, a method is provided for activating a silenced gene in a cell, comprising contacting the cell with an effective amount of a compound which is capable of inhibiting the $NAD^+$-dependent deacetylase activity of a member of the SIR2 family of proteins.

In a fourth aspect of the present invention, a method is provided for promoting p53-dependent apoptosis of a cell comprising contacting the cell with an effective amount of a compound which is capable of inhibiting the NAD⁺-dependent deacetylase activity of a member of the SIR2 family of proteins.

In a further aspect of the present invention, a method is provided for inhibiting BCL6 transcriptional repressor activity, comprising contacting a cell with an effective amount of a compound which is capable of inhibiting the NAD⁺-dependent deacetylase activity of a member of the SIR2 family of proteins.

In another aspect of the present invention, a method is provided for inhibiting the deacetylase activity of a NAD⁺-dependent deacetylase comprising contacting the NAD⁺-dependent deacetylase with a NAD⁺-dependent deacetylase inhibiting amount of a compound of Formula I:

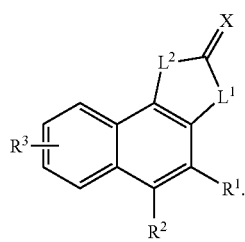

I

In Formula I, the letter X is a member selected from the group consisting of O and S. The symbols $L^1$ and $L^2$ each represent members independently selected from the group consisting of O, S, ethylene and propylene, substituted with 0-2 R groups, wherein exactly one of the symbols $L^1$ and $L^2$ represents a member selected from the group consisting of O and S. Each instance of the letter R of symbols $L^1$ and $L^2$ independently represents a member selected from the group consisting of $C_{1-6}$-alkyl, $C_{2-6}$alkenyl and —$CO_2R^4$. The symbols $R^1$ and $R^2$ each represent members independently selected from the group consisting of hydrogen, $C_{1-6}$alkoxy, $C_{0-6}$alkoxy-aryl and hydroxy. Alternatively, the symbols $R^1$ and $R^2$ are taken together with the carbons to which they are attached to form a six-membered lactone ring. The symbol $R^3$ represents a member selected from the group consisting of hydrogen, $C_{1-6}$alkyl, aryl, —$OR^4$, —$NR^4R^4$, —$CO_2R^4$, —$C(O)R^4$, —$C(O)NR^4R^4$, —CN, —$NO_2$ and halogen. Each instance of the symbol $R^4$ independently represents a member selected from the group consisting of hydrogen and $C_{1-6}$alkyl.

In a further aspect of the present invention, a method is provided for inhibiting the deacetylase activity of a NAD⁺-dependent deacetylase comprising contacting the NAD⁺-dependent deacetylase with a NAD⁺-dependent deacetylase inhibiting amount of a compound of Formula II:

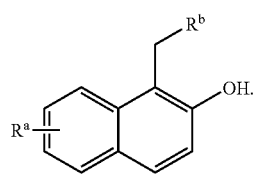

II

In Formula II, the symbol $R^a$ is a member selected from the group consisting of hydrogen, $C_{1-6}$alkyl, aryl, —$OR^e$, —$NR^e$ $R^e$, —$CO_2R^e$, —$C(O)R^e$, —$C(O)NR^eR^e$, —CN, —$NO_2$ and halogen, while the symbol $R^b$ is a member selected from the group consisting of:

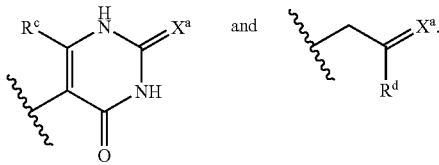

In the components above, the symbol $X^a$ represents a member selected from the group consisting of O, S and $NR^e$, while the symbol $R^c$ represents a member selected from the group consisting of hydrogen, $C_{1-6}$alkyl and aryl optionally substituted with a member selected from the group consisting of hydrogen, $C_{1-6}$alkyl, aryl, —$OR^e$, —$NR^eR^e$, —CN, —$NO_2$ and halogen. The symbol $R^d$ represents a member selected from the group consisting of hydrogen, $C_{1-6}$alkyl, aryl, —$OR^e$, —$NR^eR^e$ and halogen. And, each instance of the symbol $R^e$ independently represents a member selected from the group consisting of hydrogen and $C_{1-6}$alkyl.

In a further aspect of the present invention, a method is provided for the treatment of cancer comprising the step of administering to a subject in need of such treatment a first amount of an antineoplastic agent and a second amount of a compound of Formula I:

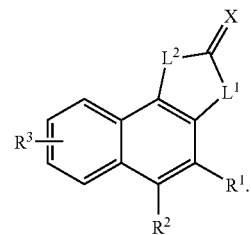

I

In Formula I, the letter X is a member selected from the group consisting of O and S. The symbols $L^1$ and $L^2$ each represent members independently selected from the group consisting of O, S, ethylene and propylene, substituted with 0-2 R groups, wherein exactly one of the symbols $L^1$ and $L^2$ represents a member selected from the group consisting of O and S. Each instance of the letter R of symbols $L^1$ and $L^2$ independently represents a member selected from the group consisting of $C_{1-6}$alkyl, $C_{2-6}$alkenyl and —$CO_2R^4$. The symbols $R^1$ and $R^2$ each represent members independently selected from the group consisting of hydrogen, $C_{1-6}$alkoxy, $C_{0-6}$alkoxy-aryl and hydroxy. Alternatively, the symbols $R^1$ and $R^2$ are taken together with the carbons to which they are attached to form a six-membered lactone ring. The symbol $R^3$ represents a member selected from the group consisting of hydrogen, $C_{1-6}$alkyl, aryl, —$OR^4$, —$NR^4R^4$, —$CO_2R^4$, —$C(O)R^4$, —$C(O)NR^4R^4$, —CN, —$NO_2$ and halogen. Each instance of the symbol $R^4$ independently represents a member selected from the group consisting of hydrogen and $C_{1-6}$alkyl.

In another aspect of the present invention, a method is provided for the treatment of cancer comprising the step of administering to a subject in need of such treatment a first amount of a an antineoplastic agent, and a second amount of a compound of Formula II:

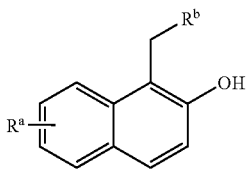

In Formula II, the symbol $R^a$ is a member selected from the group consisting of hydrogen, $C_{1-6}$alkyl, aryl, —$OR^e$, —$NR^e R^e$, —$CO_2R^e$, —$C(O)R^e$, —$C(O)NR^e R^e$, —CN, —$NO_2$ and halogen, while the symbol $R^b$ is a member selected from the group consisting of:

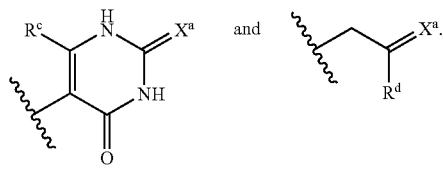

In the components above, the symbol $X^a$ represents a member selected from the group consisting of O, S and $NR^e$, while the symbol $R^c$ represents a member selected from the group consisting of hydrogen, $C_{1-6}$alkyl and aryl optionally substituted with a member selected from the group consisting of hydrogen, $C_{1-6}$alkyl, aryl, —$OR^e$, —$NR^e R^e$, —CN, —$NO_2$ and halogen. The symbol $R^d$ represents a member selected from the group consisting of hydrogen, $C_{1-6}$alkyl, aryl, —$OR^e$, —$NR^e R^e$ and halogen. And, each instance of the symbol $R^e$ independently represents a member selected from the group consisting of hydrogen and $C_{1-6}$alyl.

In yet another aspect of the present invention, a composition is provided for the treatment of cancer comprising an antineoplastic agent and a compound of Formula I:

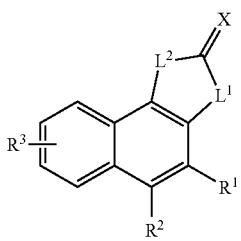

In Formula I, the letter X is a member selected from the group consisting of O and S. The symbols $L^1$ and $L^2$ each represent members independently selected from the group consisting of O, S, ethylene and propylene, substituted with 0-2 R groups, wherein exactly one of the symbols $L^1$ and $L^2$ represents a member selected from the group consisting of O and S. Each instance of the letter R of symbols $L^1$ and $L^2$ independently represents a member selected from the group consisting of $C_{1-6}$alkyl, $C_{2-6}$alkenyl and —$CO_2R^4$. The symbols $R^1$ and $R^2$ each represent members independently selected from the group consisting of hydrogen, $C_{1-6}$alkoxy, $C_{0-6}$alkoxy-aryl and hydroxy. Alternatively, the symbols $R^1$ and $R^2$ are taken together with the carbons to which they are attached to form a six-membered lactone ring. The symbol $R^3$ represents a member selected from the group consisting of hydrogen, $C_{1-6}$alkyl, aryl, —$OR^4$, —$NR^4R^4$, —$CO_2R^4$, —$C(O)R^4$, —$C(O)NR^4R^4$, —CN, —$NO_2$ and halogen. Each instance of the symbol $R^4$ independently represents a member selected from the group consisting of hydrogen and $C_{1-6}$alkyl.

In a further aspect of the present invention, a composition is provided for the treatment of cancer comprising an antineoplastic agent and a compound of Formula II:

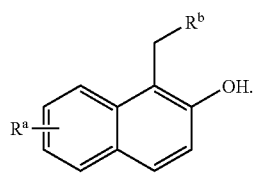

In Formula II, the symbol $R^a$ is a member selected from the group consisting of hydrogen, $C_{1-6}$alkyl, aryl, —$OR^e$, —$NR^e R^e$, —$CO_2R^e$, —$C(O)R^e$, —$C(O)NR^e R^e$, —CN, —$NO_2$ and halogen, while the symbol $R^b$ is a member selected from the group consisting of:

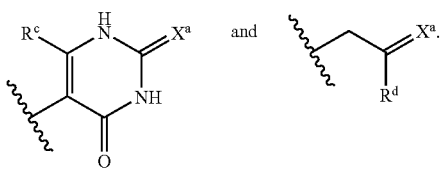

In the components above, the symbol $X^a$ represents a member selected from the group consisting of O, S and $NR^e$, while the symbol $R^c$ represents a member selected from the group consisting of hydrogen, $C_{1-6}$alkyl and aryl optionally substituted with a member selected from the group consisting of hydrogen, $C_{1-6}$alkyl, aryl, —$OR^e$, —$NR^e R^e$, —CN, —$NO_2$ and halogen. The symbol $R^d$ represents a member selected from the group consisting of hydrogen, $C_{1-6}$alkyl, aryl, —$OR^e$, —$NR^e R^e$ and halogen. And, each instance of the symbol $R^e$ independently represents a member selected from the group consisting of hydrogen and $C_{1-6}$alkyl.

In another aspect of the present invention, a pharmaceutical composition is provided, comprising a pharmaceutically acceptable excipient and a compound, and all pharmaceutically acceptable salts thereof, of Formula I:

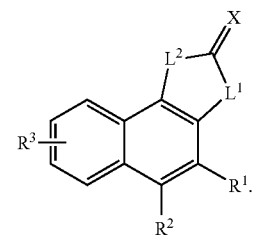

In Formula I, the letter X is a member selected from the group consisting of O and S. The symbols $L^1$ and $L^2$ each represent members independently selected from the group consisting of O, S, ethylene and propylene, substituted with 0-2 R groups, wherein exactly one of the symbols $L^1$ and $L^2$ represents a member selected from the group consisting of O and S. Each instance of the letter R of symbols $L^1$ and $L^2$ independently represents a member selected from the group consisting of $C_{1-6}$alkyl, $C_{2-6}$alkenyl and —$CO_2R^4$. The symbols $R^1$ and $R^2$ each represent members independently selected from the group consisting of hydrogen, $C_{1-6}$alkoxy, $C_{0-6}$alkoxy-aryl and hydroxy. Alternatively, the symbols $R^1$ and $R^2$ are taken together with the carbons to which they are attached to form a six-membered lactone ring. The symbol $R^3$ represents a member selected from the group consisting of hydrogen, $C_{1-6}$alkyl, aryl, —$OR^4$, —$NR^4R^4$, —$CO_2R^4$, —$C(O)R^4$, —$C(O)NR^4R^4$, —CN, —$NO_2$ and halogen. Each instance of the symbol $R^4$ independently represents a member selected from the group consisting of hydrogen and $C_{1-6}$alkyl.

In another aspect of the present invention, a pharmaceutical composition is provided, comprising a pharmaceutically acceptable excipient and a compound, and all pharmaceutically acceptable salts thereof, of Formula II:

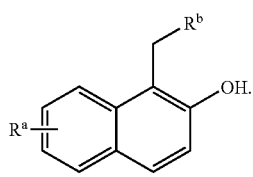

In Formula II, the symbol $R^a$ is a member selected from the group consisting of hydrogen, $C_{1-6}$alkyl, aryl, —$OR^e$, —$NR^eR^e$, —$CO_2R^e$, —$C(O)R^e$, —$C(O)NR^eR^e$, —CN, —$NO_2$ and halogen, while the symbol $R^b$ is a member selected from the group consisting of:

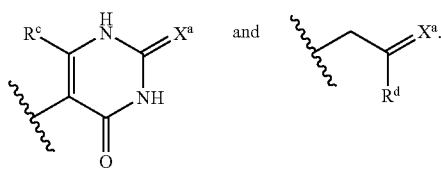

In the components above, the symbol $X^a$ represents a member selected from the group consisting of O, S and $NR^e$, while the symbol $R^c$ represents a member selected from the group consisting of hydrogen, $C_{1-6}$alkyl and aryl optionally substituted with a member selected from the group consisting of hydrogen, $C_{1-6}$alkyl, aryl, —$OR^e$, —$NR^eR^e$, —CN, —$NO_2$ and halogen. The symbol $R^d$ represents a member selected from the group consisting of hydrogen, $C_{1-6}$alkyl, aryl, —$OR^e$, —$NR^eR^e$ and halogen. And, each instance of the symbol $R^e$ independently represents a member selected from the group consisting of hydrogen and $C_{1-6}$alkyl.

BRIEF DESCRIPTION OF THE DRAWINGS

FIG. 6. Table of exemplary compounds of the present invention, and their potency for the inhibition of the $NAD^+$-dependent deacetylase activity of a member of the SIR2 family of proteins.

DETAILED DESCRIPTION OF THE INVENTION

Definitions

Figure 1:
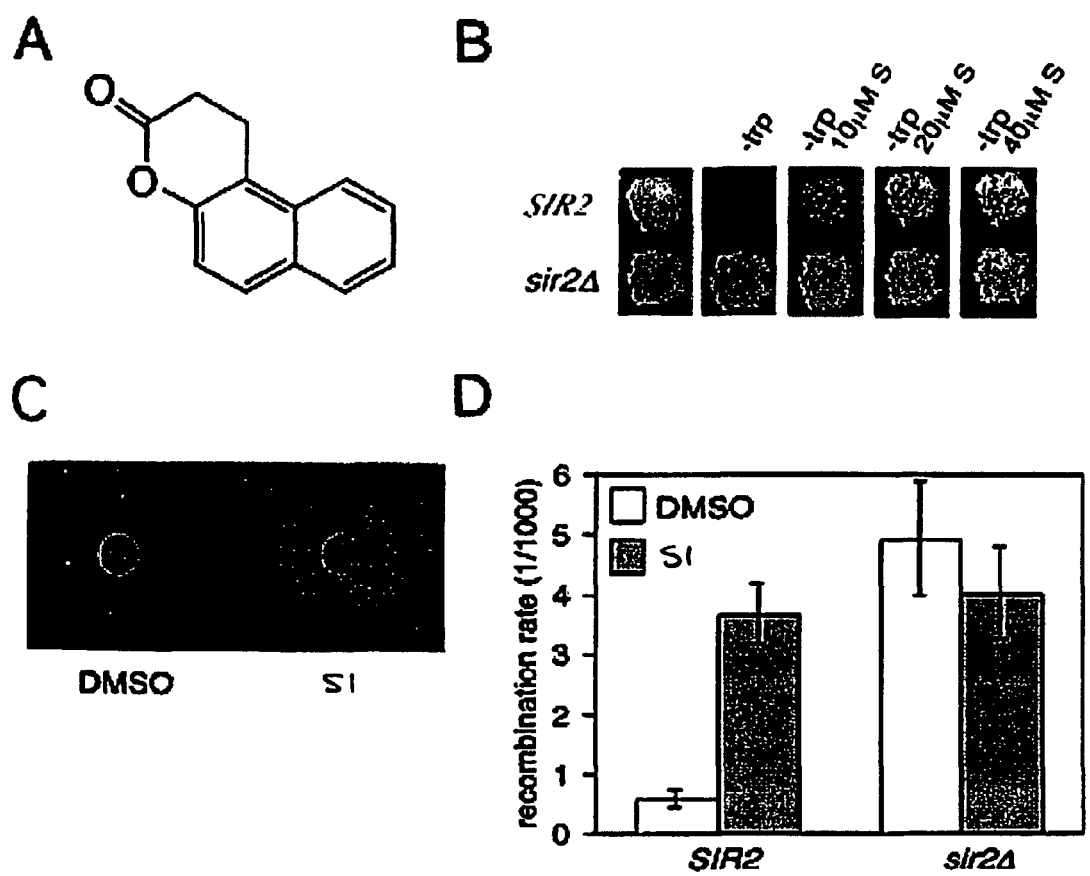
FIG. 1. (A) Chemical structure of S1. (B) Activation of a TRP1 reporter at the silent HMR mating locus by S1 (S). Wild type (SIR2) or sir2Δ cells with TRP1 integrated into HMR. Cells were replica plated onto complete synthetic media, or media lacking tryptophan (-trp) without or with the indicated concentrations of S1. (C) Loss of responsiveness to α factor in the presence of S1. The halo of cells indicates those able to grow. (D) S1 increases recombination of an ADE2 reporter integrated within ribosomal DNA array.

Unless defined otherwise, all technical and scientific terms used herein generally have the same meaning as commonly understood by one of ordinary skill in the art to which this invention belongs. Generally, the nomenclature used herein and the laboratory procedures for organic and analytical chemistry are those well known and commonly employed in the art.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below as "heteroalkyl." Preferred alkyl groups are limited to hydrocarbon groups, and may be branched- or straight-chain. More preferred alkyl groups are unsubstituted.

The term "alkylene" by itself or as part of another substituent means a divalent radical derived from an alkane, as exemplified by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quatemized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$,—S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified by —$CH_2$—$CH_2$—S—$CH_2CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon substituent which can be a single ring or multiple rings (up to three rings) which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quatemized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazol 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be a variety of groups selected from: —OR', =O, =NR', =N—OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —CN and —$NO_2$ in a number ranging from zero to (2 m'+1), where m is the total number of carbon atoms in such radical. R', R" and R'" each independently refer to hydrogen, unsubstituted ($C_1$-$C_8$)alkyl and heteroalkyl, unsubstituted aryl, aryl substituted with 1-3 halogens, unsubstituted alkyl, alkoxy or thioalkoxy groups, or aryl-($C_1$-$C_4$)alkyl groups. When R' and R" are attached to the same nitrogen atom, they can be combined with the nitrogen atom to form a 5-, 6-, or 7-membered ring. For example, —NR'R" is meant to include 1-pyrrolidinyl and 4-morpholinyl. From the above discussion of substituents, one of skill in the art will understand that the term "alkyl" is meant to include groups such as haloalkyl (e.g., —$CF_3$ and —$CH_2CF_3$) and acyl (e.g., —C(O)$CH_3$, —C(O)$CF_3$, —C(O)$CH_2OCH_3$, and the like). Preferably, substituted alkyl groups are those having 3, 2 or 1 substituents selected from the group consisting of —OR', —NR'R", -halogen, —C(O)R', —$CO_2$R', —CONR'R", —CN and —$NO_2$.

Similarly, substituents for the aryl and heteroaryl groups are varied and are selected from: -halogen, —OR', —OC(O)R', —NR'R", —SR', —R', —CN, —$NO_2$, —$CO_2$R', —CONR'R", —C(O)R', —OC(O)NR'R", —NR"C(O)R', —NR"C(O)$_2$R', —NR'—C(O)NR"R'", —NH—C(NH$_2$)=NH, —NR'C(NH$_2$)=NH, —NH—C(NH$_2$)=NR', —S(O)R', —S(O)$_2$R', —S(O)$_2$NR'R", —$N_3$, —CH(Ph)$_2$, perfluoro($C_1$-$C_4$)alkoxy, and perfluoro($C_1$-$C_4$)alkyl, in a number ranging from zero to the total number of open valences on the aromatic ring system; and where R', R" and R'" are independently selected from hydrogen, ($C_1$-$C_8$)alkyl and heteroalkyl, unsubstituted aryl and heteroaryl, (unsubstituted aryl)-($C_1$-$C_4$)alkyl, and (unsubstituted aryl)oxy-($C_1$-$C_4$)alkyl. Preferably, substituted aryl groups are those having 1, 2 or 3 substituents selected from the group consisting of -halogen, —OR', —NR'R'', —CN, —NO$_2$, —CO$_2$R', —CONR'R'', —C(O)R', —N$_3$, perfluoro(C$_1$-C$_4$)alkoxy, and perfluoro(C$_1$-C$_4$)alkyl.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$-B-, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'—, is selected from hydrogen or unsubstituted (C$_1$-C$_6$)alkyl.

As used herein, the term "heteroatom" is meant to include oxygen (O), nitrogen (N) and sulfur (S).

As used herein, the term "lactone ring" refers to a five-, six- or seven-membered cyclic ester, such as

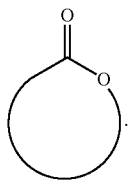

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are all intended to be encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

The term "SIR2" refers to the silent information regulator family of proteins, also known as sirtuins. This family includes both mammalian and non-mammalian proteins. For example, yeast homologues of SIR2 include, but are not limited to, HST1, HST2, HST3 and HST4. The mammalian homologues include, but are not limited to, SIRT1, SIRT2, SIRT3, SIRT4, SIRT5, SIRT6, SIRT7 and SIRT8, as well as sirtuins 1 to 8. More specific examples include, but are not limited to, Sir2p and SIR2α.

The term "NAD$^+$-dependent deacetylase" refers to a protein that removes the acetyl groups from a lysine residue of another protein, wherein the deacetylation is coupled to NAD (nicotinamide adenosine dinucleotide) cleavage.

The term "p53-dependent apoptosis" refers to the genetically determined death of a cell that is dependent on, or stimulated by, the p53 gene, a gene that typically inhibits non-natural cell growth, such as that observed in tumors.

The term "BCL6 transcriptional repressor activity" refers to the activity of the BCL6 gene that results in the repression of transcription, the process of constructing an RNA chain from a DNA template.

The terms "silence", "silencing" and "silenced" refers to a mechanism by which gene expression in particular regions of the genome are repressed.

The term "chromatin" refers to a complex mixture of nucleic acid and proteins (such as histone) in eukaryotic cells, and is usually dispersed in the interphase nucleus and condensed into chromosomes.

The term "gene" refers to any segment of DNA associated with a biological function. Thus, genes include coding sequences and/or the regulatory sequences required for their expression. Genes also include nonexpressed DNA segments that, for example, form recognition sequences for other proteins.

The term "protein" refers to series of amino acid residues connected one to the other by peptide bonds between the alpha-amino and carboxy groups of adjacent residues. In general, the term "protein" is used to designate a series of greater than 50 amino acid residues connected one to the other.

The term "antineoplastic agent" refers to a means for inhibiting or combating the undesirable growth of biological tissue. Antineoplastic agents include, but are not limited to, antiangiogenic and antivascular agents, antimetabolites, antifolates and other inhibitors of DNA synthesis, antisense oligonucleotides, biological response modifiers, DNA-alkylating agents, DNA intercalators, DNA repair agents, growth factor receptor kinase inhibitors, hormone agents, immunoconjugates, microtubule disruptors and topoisomerase I/II inhibitors. Antineoplastic agents can also include cyclophosphamide, triethylenephosphoramide, triethylenethiophosphoramide, flutamide, altretamine, triethylenemelamine, trimethylolmelamine, meturedepa, uredepa, aminoglutethimide, L-asparaginase, BCNU, benzodepa, bleomycin, busulfan, camptothecin, capecitabine, carboquone, chlorambucil, cytarabine, dactinomycin, daunomycin, daunorubicin, docetaxol, doxorubicin, epirubicin, estramustine, dacarbazine, etoposide, fluorouracil, gemcitabine, hydroxyurea, ifosfamide, improsulfan, mercaptopurine, methotrexate, mitomycin, mitotane, mitoxantrone, novembrichin, paclitaxel, piposulfan, plicamycin, prednimustine, procarbazine, tamoxifen, temozolomide, teniposide, thioguanine, thiotepa, UFT, uracil mustard, vinblastine, vincristine, vinorelbine and vindesine.

The term "cancer" refers to the uncontrolled growth of abnormal cells. Specific cancers are selected from, but not limited to, rhabdomyosarcomas, chorio carcinomas, glioblastoma multiformas (brain tumors), bowel and gastric carcinomas, leukemias, ovarian cancers, prostate cancers, lymphomas, osteosarcomas or cancers which have metastasized.

The term "genetic blood disease" refers to a hereditary disease of the blood that includes, but is not limited to, hyperproliferative diseases, thalassaemias and sickle cell disease.

The term "tumor suppressor gene" refers to a gene that acts to suppress the uncontrolled growth of a cancer, such as a tumor.

The term "ligand binding domain" refers to a region of a protein, enzyme, or gene that binds to a ligand selective for that particular site;

The terms "treating" and "treatment" refer to a method of alleviating or abating a disease and/or its attendant symptoms.

The terms "inhibition", "inhibits" and "inhibitor" refer to a method of prohibiting a specific action or function.

The term "therapeutically effective amount" refers to that amount of the compound being administered sufficient to prevent development of or alleviate to some extent one or more of the symptoms of the condition or disorder being treated.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and deleterious to the recipient thereof.

The term "subject" refers to animals such as mammals, including, but not limited to, primates (e.g., humans), cows, sheep, goats, horses, dogs, cats, rabbits, rats, mice and the like. In certain embodiments, the subject is a human.

General

The present invention involves a phenotypic screen for small molecule inhibitors of the NAD$^+$-dependent deacetylase activity of the SIR2 class of proteins. Several of the proteins in this class play an important role in the silencing of genes. In one aspect, the deacetylation of histone by a protein in the SIR2 class, can lead to the silencing of tumor suppressor genes. In another aspect, the deacetylation of the p53 tumor suppressor gene by a protein in the SIR2 class, reduces p53-dependent apoptosis. Diseases in which apoptosis is involved include diseases that are associated with an increase in cell survival due to inhibition of apoptosis, such as cancer, autoimmune diseases, inflammatory diseases and viral infections and diseases that are associated with a decrease in cell death due to hyperactive apoptosis, such as AIDS, neurodegenerative disease, hematologic diseases, and tissue damage. A further aspect of the present invention relates to the acetylation of BCL6 by inhibiting the deacetylase activity of a protein in the SIR2 class. Doing so prevents expression of differentiation genes in B-cell non-Hodgkin lymphoma (B-NHL) and diffused large B-cell lymphomas (DLBCL). Therefore, inhibiting the NAD$^+$-dependent deacetylase activity of a protein in the SIR2 family of proteins leads to the activation of p53 and either growth or arrest of apoptosis, it is possible to treat various cancers and disease states that are well-known to one of skill in the art.

EMBODIMENTS OF THE INVENTION

Methods

In view of the surprising discovery above, the present invention provides in one aspect a method is provided for identifying compounds useful for the treatment of cancer or genetic blood diseases, comprising the step of determining whether the compound inhibits the deacetylase activity of a NAD$^+$-dependent deacetylase. In a related aspect of the present invention, the method for treating cancer or genetic blood diseases comprises the step of administering to a subject in need thereof, a therapeutically effective amount of a compound that inhibits the deacetylase activity of a NAD$^+$-dependent deacetylase.

In a preferred aspect of the present invention, the identified compounds are useful for the treatment of silenced tumor suppressor genes, B-cell-derived non-Hodgkin lymphomas and diffuse large B-cell lymphomas. In another preferred aspect of the present invention, the identified compounds are useful for the treatment of thalassaemias and sickle cell disease.

In a further preferred aspect of the present invention, the step of determining comprises the step of specifically binding radiolabelled (1,2-dihydro-3H-naphtho[2,1-b]pyran-3-one) to the ligand binding domain of a member of the SIR2 family of proteins.

In another preferred aspect of the present invention, the NAD+-dependent deacetylase is a member of the SIR2 family of proteins. In a more preferred aspect, the member of the SIR2 family of proteins is selected from the group consisting of Sir2p and SIR2α. In a most preferred aspect, the member of the SIR2 family of proteins is SIR2α.

In another aspect of the present invention, a method is provided for identifying compounds which will be useful for the treatment of cancer or genetic blood diseases, comprising the step of determining whether the compound inhibits the NAD+-dependent deacetylase activity of a member of the SIR2 family of proteins. In a preferred aspect of the present invention, the method for treating cancer or genetic blood diseases comprises the step of administering to a subject in thereof, a therapeutically effective amount of a compound that inhibits the NAD+-dependent deacetylase activity of a member of the SIR2 family of proteins.

In another preferred aspect of the present invention, a method is provided for activating a silenced gene in a cell, comprising contacting the cell with an effective amount of a compound which is capable of inhibiting the NAD+-dependent deacetylase activity of a member of the SIR2 family of proteins.

In still another preferred aspect of the present invention, a method is provided for promoting p53-dependent apoptosis of a cell comprising contacting the cell with an effective amount of a compound which is capable of inhibiting the NAD+-dependent deacetylase activity of a member of the SIR2 family of proteins.

In a further aspect of the present invention, a method is provided for inhibiting BCL6 transcriptional repressor activity, comprising contacting a cell with an effective amount of a compound which is capable of inhibiting the NAD+-dependent deacetylase activity of a member of the SIR2 family of proteins.

In another aspect of the present invention, a method is provided for inhibiting the deacetylase activity of a NAD+-dependent deacetylase comprising contacting the NAD+-dependent deacetylase with a NAD+-dependent deacetylase inhibiting amount of a compound of Formula I:

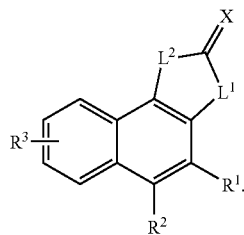

I

In Formula I, the letter X is a member selected from the group consisting of O and S. The symbols $L^1$ and $L^2$ each represent members independently selected from the group consisting of O, S, ethylene and propylene, substituted with 0-2 R groups, wherein exactly one of the symbols $L^1$ and $L^2$ represents a member selected from the group consisting of O and S. Each instance of the letter R of symbols $L^1$ and $L^2$ independently represents a member selected from the group consisting of $C_{1-6}$alkyl, $C_{2-6}$alkenyl and —$CO_2R^4$. The symbols $R^1$ and $R^2$ each represent members independently selected from the group consisting of hydrogen, $C_{1-6}$alkoxy, $C_{0-6}$alkoxy-aryl and hydroxy. Alternatively, the symbols $R^1$ and $R^2$ are taken together with the carbons to which they are attached to form a six-membered lactone ring. The symbol $R^3$ represents a member selected from the group consisting of hydrogen, $C_{1-6}$alkyl, aryl, —$OR^4$, —$NR^4R^4$, —$CO_2R^4$, —$C(O)R^4$, —$C(O)NR^4R^4$, —CN, —$NO_2$ and halogen. Each instance of the symbol $R^4$ independently represents a member selected from the group consisting of hydrogen and $C_{1-6}$alkyl.

In a preferred aspect of the present invention, the compound of Formula I has the following structure:

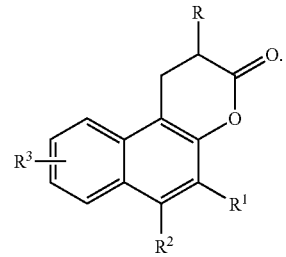

In this case, the symbol $R^1$ is a member selected from the group consisting of hydrogen, $C_{1-6}$alkoxy and $C_{0-6}$alkoxy-aryl; the symbol $R^2$ is a member selected from the group consisting of hydrogen and hydroxy; the symbol $R^3$ is a member selected from the group consisting of hydrogen and —$OR^4$; and the symbol $R^4$ is $C_{1-6}$alkyl.

In another preferred aspect of the present invention, the symbol $R^1$ is a member selected from the group consisting of $C_{1-6}$alkoxy, $C_{0-6}$alkoxy-aryl and hydroxy. In a more preferred aspect of the present invention, the symbol $R^1$ is a member selected from the group consisting of hydroxy, methoxy and benzyloxy. In a most preferred aspect of the present invention, the symbol $R^1$ is benzyloxy. In another preferred embodiment, the term aryl is a member selected from the group consisting of phenyl and naphthyl.

In another aspect of the present invention, a method is provided for inhibiting the deacetylase activity of a NAD+-dependent deacetylase comprising contacting the NAD+-dependent deacetylase with a NAD+-dependent deacetylase inhibiting amount of a compound of Formula II:

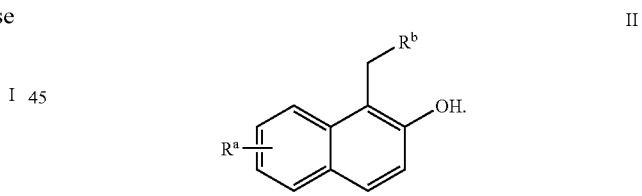

II

In Formula II, the symbol $R^a$ is a member selected from the group consisting of hydrogen, $C_{1-6}$alkyl, aryl, —$OR^e$, —$NR^eR^e$, —$CO_2R^e$, —$C(O)R^e$, —$C(O)NR^eR^e$, —CN, —$NO_2$ and halogen, while the symbol $R^b$ is a member selected from the group consisting of:

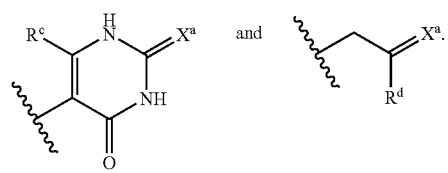

In the components above, the symbol $X^a$ represents a member selected from the group consisting of O, S and $NR^e$, while the symbol $R^c$ represents a member selected from the group consisting of hydrogen, $C_{1-6}$alkyl and aryl optionally substituted with a member selected from the group consisting of hydrogen, $C_{1-6}$alkyl, aryl, —$OR^e$, —$NR^eR^e$, —CN, —$NO_2$ and halogen. The symbol $R^d$ represents a member selected from the group consisting of hydrogen, $C_{1-6}$alkyl, aryl, —$OR^e$, —$NR^eR^e$ and halogen. And, each instance of the symbol $R^e$ independently represents a member selected from the group consisting of hydrogen and $C_{1-6}$alkyl.

In a preferred aspect of the present invention, Formula II has the following structure:

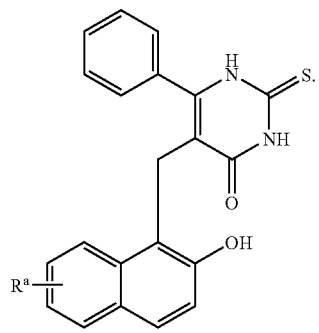

In a further aspect of the present invention, a method is provided for the treatment of cancer comprising administering to a subject in need of such treatment a first amount of an antineoplastic agent and a second amount of a compound of Formula I:

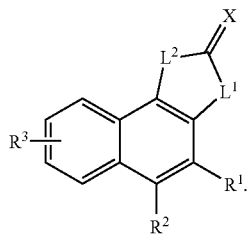

In Formula I, the letter X is a member selected from the group consisting of O and S. The symbols $L^1$ and $L^2$ each represent members independently selected from the group consisting of O, S, ethylene and propylene, substituted with 0-2 R groups, wherein exactly one of the symbols $L^1$ and $L^2$ represents a member selected from the group consisting of O and S. Each instance of the letter R of symbols $L^1$ and $L^2$ independently represents a member selected from the group consisting of $C_{1-6}$alkyl, $C_{2-6}$alkenyl and —$CO_2R^4$. The symbols $R^1$ and $R^2$ each represent members independently selected from the group consisting of hydrogen, $C_{1-6}$alkoxy, $C_{0-6}$alkoxy-aryl and hydroxy. Alternatively, the symbols $R^1$ and $R^2$ are taken together with the carbons to which they are attached to form a six-membered lactone ring. The symbol $R^3$ represents a member selected from the group consisting of hydrogen, $C_{1-6}$alkyl, aryl, —$OR^4$, —$NR^4R^4$, —$CO_2R^4$, —$C(O)R^4$, —$C(O)NR^4R^4$, —CN, —$NO_2$ and halogen. Each instance of the symbol $R^4$ independently represents a member selected from the group consisting of hydrogen and $C_{1-6}$alkyl.

In another aspect of the present invention, a method is provided for the treatment of cancer comprising administering to a subject in need of such treatment a first amount of an antineoplastic agent, and a second amount of a compound of Formula II:

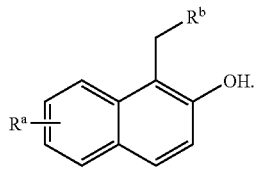

In Formula II, the symbol $R^a$ is a member selected from the group consisting of hydrogen, $C_{1-6}$alkyl, aryl, —$OR^e$, —$NR^eR^e$, —$CO_2R^e$, —$C(O)R^e$, —$C(O)NR^eR^e$, —CN, —$NO_2$ and halogen, while the symbol $R^b$ is a member selected from the group consisting of:

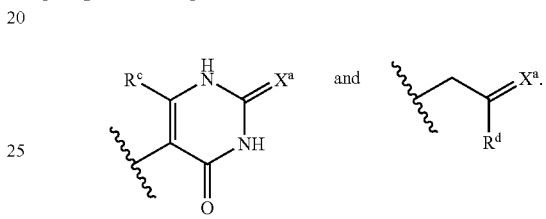

In the components above, the symbol $X^a$ represents a member selected from the group consisting of O, S and $NR^e$, while the symbol $R^c$ represents a member selected from the group consisting of hydrogen, $C_{1-6}$alkyl and aryl optionally substituted with a member selected from the group consisting of hydrogen, $C_{1-6}$alkyl, aryl, —$OR^e$, —$NR^eR^e$, —CN, —$NO_2$ and halogen. The symbol $R^d$ represents a member selected from the group consisting of hydrogen, $C_{1-6}$alkyl, aryl, —$OR^e$, —$NR^eR^e$ and halogen. And, each instance of the symbol $R^e$ independently represents a member selected from the group consisting of hydrogen and $C_{1-6}$alkyl.

Compositions

In yet another aspect of the present invention, a composition is provided for the treatment of cancer comprising an antineoplastic agent and a compound of Formula I:

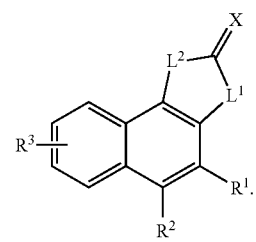

In Formula I, the letter X is a member selected from the group consisting of O and S. The symbols $L^1$ and $L^2$ each represent members independently selected from the group consisting of O, S, ethylene and propylene, substituted with 0-2 R groups, wherein exactly one of the symbols $L^1$ and $L^2$ represents a member selected from the group consisting of O and S. Each instance of the letter R of symbols $L^1$ and $L^2$ independently represents a member selected from the group consisting of $C_{1-6}$alkyl, $C_{2-6}$alkenyl and —$CO_2R^4$. The symbols $R^1$ and $R^2$ each represent members independently selected from the group consisting of hydrogen, $C_{1-6}$alkoxy, $C_{0-6}$alkoxy-aryl and hydroxy. Alternatively, the symbols $R^1$ and $R^2$ are taken together with the carbons to which they are attached to form a six-membered lactone ring. The symbol $R^3$ represents a member selected from the group consisting of hydrogen, $C_{1-6}$alkyl, aryl, —$OR^4$, —$NR^4R^4$, —$CO_2R^4$, —$C(O)R^4$, —$C(O)NR^4R^4$, —CN, —$NO_2$ and halogen. Each instance of the symbol $R^4$ independently represents a member selected from the group consisting of hydrogen and $C_{1-6}$alkyl.

In a further aspect of the present invention, a composition is provided for the treatment of cancer comprising an antineoplastic agent and a compound of Formula II:

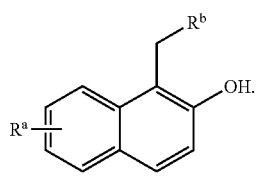

II

In Formula II, the symbol $R^a$ is a member selected from the group consisting of hydrogen, $C_{1-6}$alkyl, aryl, —$OR^e$, —$NR^eR^e$, —$CO_2R^e$, —$C(O)R^e$, —$C(O)NR^eR^e$, —CN, —$NO_2$ and halogen, while the symbol $R^b$ is a member selected from the group consisting of:

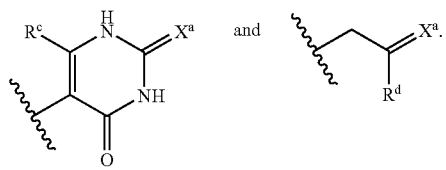

In the components above, the symbol $X^a$ represents a member selected from the group consisting of O, S and $NR^e$, while the symbol $R^c$ represents a member selected from the group consisting of hydrogen, $C_{1-6}$alkyl and aryl optionally substituted with a member selected from the group consisting of hydrogen, $C_{1-6}$alkyl, aryl, —$OR^e$, —$NR^eR^e$, —CN, —$NO_2$ and halogen. The symbol $R^d$ represents a member selected from the group consisting of hydrogen, $C_{1-6}$alkyl, aryl, —$OR^e$, —$NR^eR^e$ and halogen. And, each instance of the symbol $R^e$ independently represents a member selected from the group consisting of hydrogen and $C_{1-6}$alkyl.

In a preferred aspect of the present invention, the antineoplastic agent is a member selected from the group consisting of antiangiogenic and antivascular agents, antimetabolites, antifolates and other inhibitors of DNA synthesis, antisense oligonucleotides, biological response modifiers, DNA-alkylating agents, DNA intercalators, DNA repair agents, growth factor receptor kinase inhibitors, hormone agents, immunoconjugates, microtubule disruptors and topoisomerase I/II inhibitors.

In another preferred aspect of the present invention, the antineoplastic agent is a member selected from the group consisting of cyclophosphamide, triethylenephosphoramide, triethylenethiophosphoramide, flutamide, altretamine, triethylenemelamine, trimethylolmelamine, meturedepa, uredepa, aminoglutethimide, L-asparaginase, BCNU, benzodepa, bleomycin, busulfan, camptothecin, capecitabine, carboquone, chlorambucil, cytarabine, dactinomycin, daunomycin, daunorubicin, docetaxol, doxorubicin, epirubicin, estramustine, dacarbazine, etoposide, fluorouracil, gemcitabine, hydroxyurea, ifosfamide, improsulfan, mercaptopurine, methotrexate, mitomycin, mitotane, mitoxantrone, novembrichin, paclitaxel, piposulfan, plicamycin, prednimustine, procarbazine, tamoxifen, temozolomide, teniposide, thioguanine, thiotepa, UFT, uracil mustard, vinblastine, vincristine, vinorelbine and vindesine.

In a further preferred aspect of the present invention, the antineoplastic agent is administered after the compound. In another preferred aspect, the antineoplastic agent is administered simultaneously with the compound. In yet another preferred aspect, the antineoplastic agent is administered prior to the compound.

In another aspect of the present invention, a pharmaceutical composition is provided, comprising a pharmaceutically acceptable excipient and a compound, and all pharmaceutically acceptable salts thereof, of Formula I:

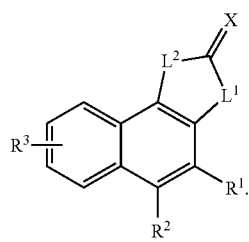

I

In Formula I, the letter X is a member selected from the group consisting of O and S. The symbols $L^1$ and $L^2$ each represent members independently selected from the group consisting of O, S, ethylene and propylene, substituted with 0-2 R groups, wherein exactly one of the symbols $L^1$ and $L^2$ represents a member selected from the group consisting of O and S. Each instance of the letter R of symbols $L^1$ and $L^2$ independently represents a member selected from the group consisting of $C_{1-6}$alkyl, $C_{2-6}$alkenyl and —$CO_2R^4$. The symbols $R^1$ and $R^2$ each represent members independently selected from the group consisting of hydrogen, $C_{1-6}$alkoxy, $C_{0-6}$alkoxy-aryl and hydroxy. Alternatively, the symbols $R^1$ and $R^2$ are taken together with the carbons to which they are attached to form a six-membered lactone ring. The symbol $R^3$ represents a member selected from the group consisting of hydrogen, $C_{1-6}$alkyl, aryl, —$OR^4$, —$NR^4R^4$, —$CO_2R^4$, —$C(O)R^4$, —$C(O)NR^4R^4$, —CN, —$NO_2$ and halogen. Each instance of the symbol $R^4$ independently represents a member selected from the group consisting of hydrogen and $C_{1-6}$alkyl.

In a preferred aspect of the present invention, the compound of Formula I has the following structure:

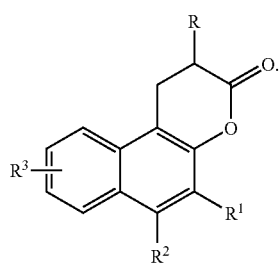

In this case, the symbol $R^1$ is a member selected from the group consisting of hydrogen, $C_{1-6}$alkoxy and $C_{0-6}$alkoxy-aryl; the symbol $R^2$ is a member selected from the group consisting of hydrogen and hydroxy; the symbol $R^3$ is a member selected from the group consisting of hydrogen and —$OR^4$; and the symbol $R^4$ is $C_{1-6}$alkyl.

In another preferred aspect of the present invention, the symbol $R^1$ is a member selected from the group consisting of $C_{1-6}$alkoxy, $C_{0-6}$alkoxy-aryl and hydroxy. In a more preferred aspect of the present invention, the symbol $R^1$ is a member selected from the group consisting of hydroxy, methoxy and benzyloxy. In a most preferred aspect of the present invention, the symbol $R^1$ is benzyloxy. In another preferred embodiment, the term aryl is a member selected from the group consisting of phenyl and naphthyl.

In another aspect of the present invention, a pharmaceutical composition is provided, comprising a pharmaceutically acceptable excipient and a compound, and all pharmaceutically acceptable salts thereof, of Formula II:

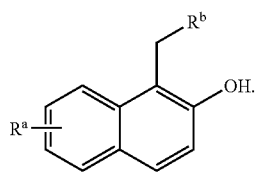

In Formula II, the symbol $R^a$ is a member selected from the group consisting of hydrogen, $C_{1-6}$alkyl, aryl, —$OR^e$, —$NR^eR^e$, —$CO_2R^e$, —$C(O)R^e$, —$C(O)NR^eR^e$, —CN, —$NO_2$ and halogen, while the symbol $R^b$ is a member selected from the group consisting of:

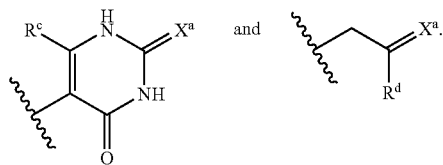

In the components above, the symbol $X^a$ represents a member selected from the group consisting of O, S and $NR^e$, while the symbol $R^c$ represents a member selected from the group consisting of hydrogen, $C_{1-6}$alkyl and aryl optionally substituted with a member selected from the group consisting of hydrogen, $C_{1-6}$alkyl, aryl, —$OR^e$, —$NR^eR^e$, —CN, —$NO_2$ and halogen. The symbol $R^d$ represents a member selected from the group consisting of hydrogen, $C_{1-6}$alkyl, aryl, —$OR^e$, —$NR^eR^e$ and halogen. And, each instance of the symbol $R^e$ independently represents a member selected from the group consisting of hydrogen and $C_{1-6}$alkyl.

In a preferred aspect of the present invention, Formula II has the following structure:

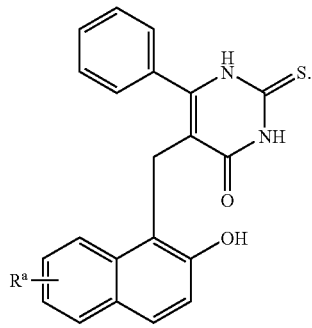

Administration

An effective amount of the composition will be determined by the existence, nature, and extent of any adverse side-effects that accompany the administration of the composition; the LD50 of the composition; and the side-effects of the composition at various concentrations. Typically, the amount of the composition administered will range from about 0.01 to about 20 mg per kg, more typically about 0.05 to about 15 mg per kg, even more typically about 0.1 to about 10 mg per kg body weight.

The compositions can be administered, for example, by intravenous infusion, orally, intraperitoneally, or subcutaneously. Oral administration is the preferred method of administration. The formulations of compounds can be presented in unit-dose or multi-dose sealed containers, such as ampoules and vials.

The compositions of the present invention are typically formulated with a pharmaceutically acceptable carrier before administration to an individual or subject. Pharmaceutically acceptable carriers are determined, in part, by the particular composition being administered, as well as by the particular method used to administer the composition. Accordingly, there are a wide variety of suitable formulations of pharmaceutical compositions of the present invention (see, e.g., Remington's Pharmaceutical Sciences, 17th ed., 1989).

Formulations suitable for oral administration can consist of (a) liquid solutions, such as an effective amount of the compound of Formula I or Formula II, suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of the following: lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The compositions of the present invention may be in formulations suitable for other routes of administration, such as, for example, intravenous infusion, intraperitoneally, or subcutaneously. The formulations include, for example, aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Injection solutions and suspensions can be prepared from sterile powders, granules, and tablets.

The dose administered to a patient, in the context of the present invention should be sufficient to effect a beneficial therapeutic response in the patient over time. For example, if the compositions of the present invention are administered to treat or prevent cancer, such as a tumor, the dose administered to the patient should be sufficient to prevent, retard, or reverse tumor growth. The dose will be determined by the efficacy of the particular composition employed and the condition of the patient, as well as the body weight or surface area of the patient to be treated. The size of the dose also will be determined by the existence, nature, and extent of any adverse side-effects that accompany the administration of a particular composition in a particular patient.

EXAMPLES

Compounds

The compounds of the present invention can be synthesized by several methods known to one of skill in the art. Methods for preparing the S1 and S2 scaffolds are shown below by way of example, and are by no means comprehensive of the methods that can be used to synthesize the compounds of the present invention. One of skill in the art will appreciate that the starting material, the reagants and the reactions shown in the schemes below, can be appropriately modified in order to synthesize all the compounds of the present invention. The appropriate modifications are known to those of skill in the art.

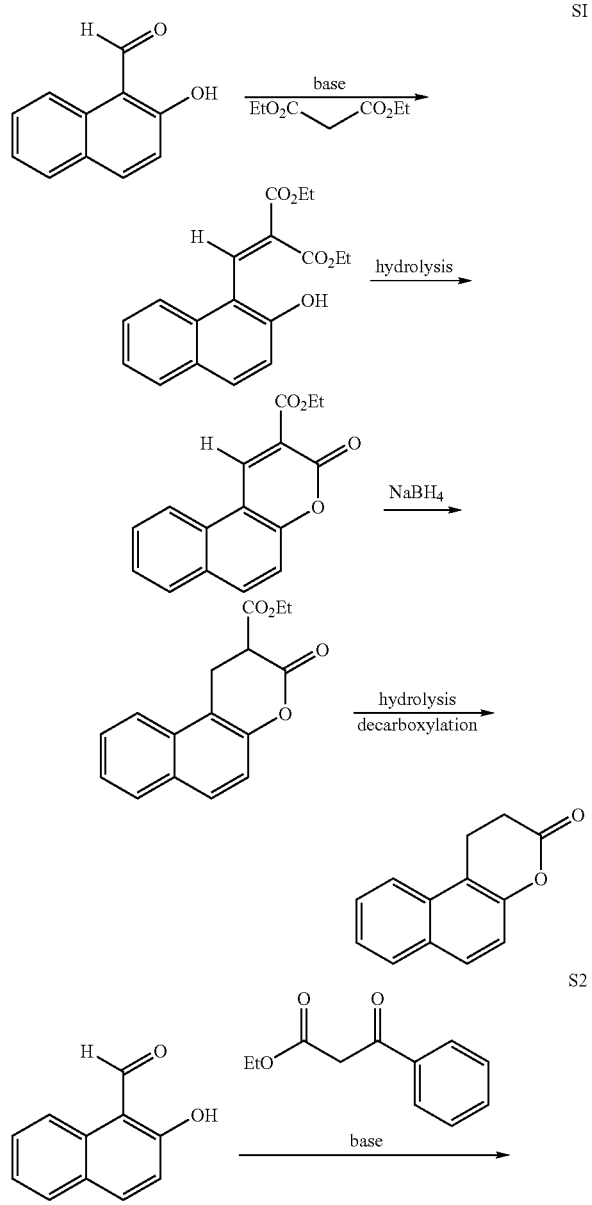

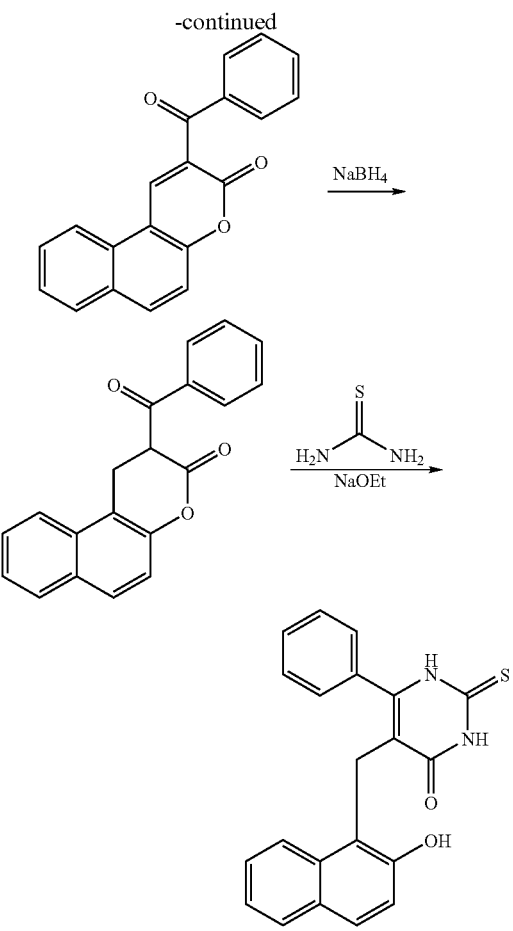

Yeast Media

All strains can be grown in synthetic complete media (SC) or selective synthetic drop-out media containing 2% glucose.

Cell-Based Chemical Screen for the Sir2p Inhibitors: Inhibition of Silencing Assays.

In order to find inhibitors of the deacetylase activity of Sir2p, screening was carried out to identify compounds that perturbed silencing at each of the loci at which Sir2p is known to act in *S. cerevisiae*: telomeres, HML, HMR, and the rDNA. The cell-based positive selection screen was designed so that inhibition of Sir2p activity permitted normal cell growth in order to avoid identifying cytotoxic compounds. Briefly, a yeast strain containing a marker gene, such as a nutritional marker, in close proximity to a telomeres in *S. cerevisiae* such that it is repressed by telomeric chromatin, is exposed to a test compound or set of test compounds dissolved in DMSO and cultured under suitable conditions and in media supplemented to permit growth only under conditions in which the marker gene is expressed. After a suitable interval, the optical density of the culture is measured. An increase in optical density corresponds to growth indicating a perturbation of silencing of the marker gene. All strains in this and other examples herein can be grown in synthetic complete media (SC) or selective synthetic drop-out media containing 2% glucose.

Initial screening for compounds that effect silencing was carried out using a URA3 assay. When the URA3 gene is in close proximity to a telomere in *S. cerevisiae*, it is repressed by telomeric chromatin (Gottschling, D. E., et al. (1990) *Cell* 63, 751-62). Because Ura3p is required for uracil biosynthesis, cells with the silenced telomeric URA3 gene are unable to grow in media lacking uracil. Accordingly, genetic perturbation of silencing activates URA3 expression and enables cells to grow in the absence of uracil (Singer, M. S., et al., (1998) *Genetics* 150, 613-3). Briefly, drug screening was performed in 96-well plates. Each well is inoculated with 150 µL of yeast culture (strain: UCC2210 MATα pprl adh4::URA3::TEL (VII-L)), containing $1 \times 10^5$ cell/ml in uracil-deficient media. A library of 6000 compounds from the NCI repository was screened for those that disrupted telomeric silencing. The compounds dissolved in DMSO are applied at three different concentrations: 0.5, 5 and 50 µM. Cultures are incubated for 36-48 h and growth in individual wells is tested by optical density ($OD_{660}$) measurements and visual inspection. Eleven compounds identified in this primary screen were analyzed further to determine whether silencing at the HML and HMR loci was also affected.

A secondary screening of the eleven identified compounds was carried out using a TRP1 gene which utilized a yeast strain with a TRP1 gene integrated at the silent HMR locus cannot grow in media lacking tryptophan (Buck, S. W. & Shore, D. (1995) *Genes Dev.* 9, 370-84). Using the method essentially described above, wells in a 96-well plate were inoculated with 150 µL of yeast culture (a yeast strain with a TRP1 gene integrated at the silent HMR locus), containing $1 \times 10^5$ cell/ml in tryptophan-deficient media. The eleven compounds dissolved in DMSO were added to the cells and the cultures are incubated for 36-48 h and growth in individual wells is tested by optical density ($OD_{660}$) measurements and visual inspection. In this assay, one of the eleven compounds enabled cells to grow in media lacking tryptophan (FIG. 1B), indicating loss of silencing at HMR. This compound (1,2-dihydro-3H-naphtho[2,1-b]pyran-3-one, FIG. 1A), hereafter referred to as S1, also disrupted silencing at HML.

Effect of S1 on silencing at the HMLα locus in MATa cells.

In one assay to confirm that S1 was capable of inhibiting silencing in vivo, a pheromone response assay was carried out. When haploid MATa cells are exposed to the mating pheromone a factor, they arrest in G1 phase of the cell cycle. Loss of silencing at the HMLα locus in MATa cells results in expression of a mating type genes (Marsh, L., et al. (1991) *Annu. Rev. Cell Biol.* 7, 699-728). The coexpression of α and a genes creates a pseudo-diploid state: cells are immune to a factor and unable to mate. In the presence of S1, MATa cells lost responsiveness to α factor (FIG. 1C) and were defective for mating. Thus, treatment with S1 disrupted silencing at HML, HMR, and telomeric loci.

Effect of S1 on Recombination at the rDNA locus.

Sir2p is involved in the silencing of rDNA through a protein complex known as RENT (regulator of nuclear silencing and telophase exit), which does not include Sir3p or Sir4p and acts at the ribosomal RNA gene cluster (rDNA). Silencing within the rDNA locus is manifested in two ways. It can weakly repress expression of an inserted reporter gene (Smith, J. S. & Boeke, J. D. (1997) *Genes Dev.* 11, 241-54), and it reduces recombination between tandem copies of the ribosomal RNA genes (Gottlieb, S. & Esposito, R. E. (1989) *Cell* 56, 771-6). Recombination was analyzed by measuring the loss rate of an ADE2 gene integrated into the rDNA array essentially as described by Kaeberlein, M., et al. (1999 *Genes Dev.* 13, 2570-80). A logarithmic culture of a yeast strain containing an ADE2 gene integrated into the rDNA array was exposed to 15 µM of S1 or DMSO for six hours. After six hours, the cultures were plated onto rich medium and the loss of expression of the ADE2 gene was measured and scored by the development of sectored red colonies. The results showed that S1 disrupted silencing of a reporter gene within the rDNA locus, just as it did at telomeres and the HM loci. Treatment with SI increased recombination rate at the rDNA locus seven-fold, which is similar to rates observed in a sir2 mutant (FIG. 1D). There was no effect on rDNA recombination in sir2 cells treated with the compound, indicating that S1 was acting specifically through the SIR2 pathway.

Whole Gene Array Analysis For Transcriptional Profiling.

In addition to SIR2, the *S. cerevisiae* genome encodes four SIR2 homologues: HST1-4 (Homologue of Sir Two) (Brachmann, C. B., et al. (1995) *Genes Dev.* 9, 2888-902). Hst2p is located in the cytoplasm and is responsible for virtually all the $NAD^+$-dependent deacetylase activity detected in a cellular lysate (Smith, J. S., et al., (2000) *Proc. Natl. Acad. Sci. USA* 97, 6658-63). Its relevant biological substrate is unknown. Hst1p is required for transcriptional repression of meiotic genes (Xie, J., et al. (1999) *EMBO J.* 18, 6448-54), whereas little is known about the cellular function of Hst3p or Hst4p. In order to determine whether the anti-silencing effects of S1 were mediated solely by Sir2p, and whether S1 affected any of the Hst proteins, the expression profile of wild type cells grown in the presence of S1 was compared to that of sir2, hst1, hst2, hst3 or hst4 deletion mutants by whole genome DNA microarray analysis.

Strains for the DNA array experiments for the whole genome analysis were obtained from Research Genetics (wild type BY4741: MATa his3, leu2, met15, ura4 or isogenic sir2, hst1, hst2, hst3 and hst4 deletion mutants). Several colonies from fresh cultures were inoculated into synthetic complete medium with 2% glucose, grown overnight at 30° C., diluted to $0.5-1 \times 10^6$ cell/ml and grown for an additional 6-9 hours until reaching a density of $0.5-1 \times 10^7$ cells/ml. For experiments with S1, drug or the solvent (DMSO) was added at the beginning of the final 9-hour growth phase. In experiments with cycloheximide, cells were treated with 50 µg/ml of cycloheximide for 40 minutes prior to the addition of S1. Total RNA was extracted using the hot acid phenol method. Microarray construction and hybridization protocols were modified from those described elsewhere (DeRisi, J. L. et al. (1997) *Science* 278, 680-6). Briefly, yeast microarrays were constructed employing a set of ~6200 or specific PCR primer pairs (Research Genetics, Huntsville, Ala.), which were used to amplify each open reading frame (orf) of the yeast genome. Individual PCR products were verified as unique via gel electrophoresis and purified using ARRAYIT 96-well PCR purification kits (TeleChem International, Sunnyvale, Calif.). Purified PCR products were mechanically "spotted" in 3×SSC (450 mM sodium chloride and 45 mM sodium citrate, pH 7.0) onto poly-lysine coated microscope slides using an OMNIGRID high-precision robotic gridder (GeneMachines, San Carlo, Calif.).

The protocol used for cDNA labeling is a modification of a protocol described elsewhere Briefly, labeled cDNA targets were prepared by reverse transcription of 30 .mu.g total RNA using oligo dT(18) primer in the presence of 0.2 mM 5-(3-aminoallyl)-2'-deoxyuridine-5'-triphosphate (aa-dUTP; Sigma-Aldrich Company, St. Louis, Mo.), 0.3 mM dTTP, and 0.5 mM each of dATP, dCTP, and dGTP. Following cDNA synthesis, either Cy3 or Cy5 mono-reactive fluors (Amersham Life Sciences, Arlington Heights, Ill.) were covalently coupled to the cDNA-incorporated aminoallyl linker in the presence of 50 mM sodium bicarbonate (pH 9.0). Two color expression profiles were generated using microarrays in which reference and experimental cDNA targets were labeled with different fluors. Following co-hybridization to the chip, a fluorescent image of the microarray was collected at both emission wavelengths using a GenePix 4000 fluorescent scanner (Axon Instruments, Inc., Foster City, Calif.) and image analysis is performed using GenePix Pro Microarray Acquisition and Analysis Software.

Three competitive hybridizations for each experimental group (sir2, hst1, hst2, hst3 and hst4 versus wild type, S1 treated wild type versus wild type and S1 plus cycloheximide versus cycloheximide alone) were performed using three separate cultures and $\log_2$ of the expression ratio calculated for every ORF. To assess the intrinsic variation of expression level for different ORF's, nine wild type versus wild type hybridizations were performed using nine separate cultures. Student t-test was used to assess if the difference between the $\log_2$ of the expression ratio for ORF in the experimental and control group (wild type versus wild type) was significant.

Figure 2:
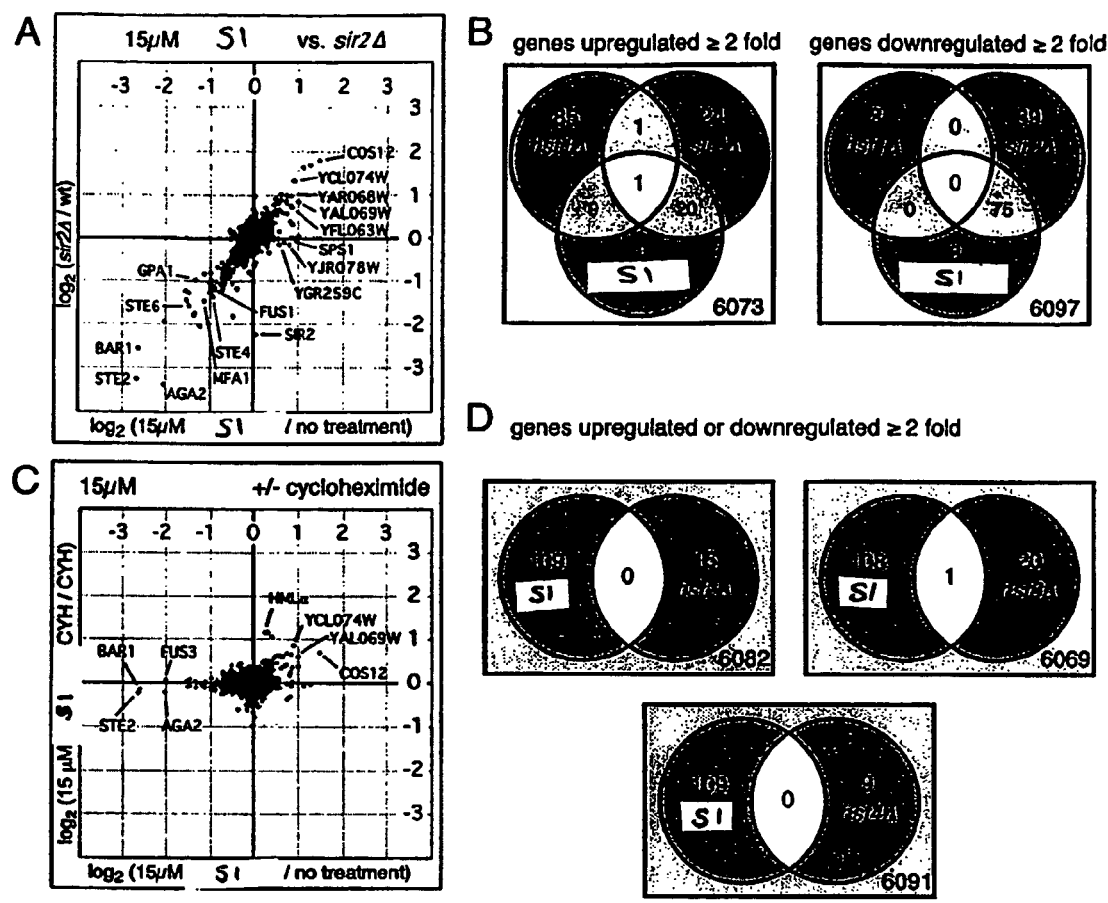
FIG. 2. S1-treated wild type (wt) cells and sir2Δ cells display similar transcriptional changes relative to untreated wt cells. (A) Correlation of transcriptional changes between genetic and chemical inactivation of Sir2p. The correlation plot shows transcriptional changes in a sir2Δ mutant relative to wt (sir2Δ/wt) on the vertical axis and changes in wt cells treated with S1 relative to untreated wt cells (15 μM S1/no treatment) on the horizontal axis. (B) A Venn diagram comparing genes up-regulated (LEFT) and down-regulated (RIGHT) more than 2-fold relative to wt or untreated cells and sir2Δ, hst1Δ or S1-treated wt cells. (C) Correlation of transcriptional changes in wt cells in response to S1 treatment with and without cycloheximide. The correlation plot shows transcriptional changes in a S1 and cycloheximide-treated wt cells relative to cells treated with cycloheximide alone (15 μM S1 CYH/CYH) on the vertical axis and changes in wt cells treated with S1 relative to untreated wt cells (15 μM S1/no treatment) on the horizontal axis. (D) Venn diagrams comparing transcriptional changes (up- or down-regulation) in hst2Δ, hst3Δ, hst4Δ cells and S1-treated cells (split).

Using this array method, the transcriptional effects of S1 correlated most highly with those of a sir2 mutation (correlation coefficient 0.748, FIG. 2A). Genes adjacent to telomeres such as COS12, and the α1 and α2 genes from the HML locus, were significantly up-regulated in both conditions (FIG. 2A). The expression of MATa-specific (e.g. MFA1, STE2, STE6, BAR1) and haploid-specific genes (e.g. FUS1, STE5) was down-regulated in both S1 treated cells and in sir2 cells (FIGS. 2, A and B). S1 also up-regulated a small number of genes that were not altered in sir2 cells, including meiosis specific genes (e.g. SPS1) which appear to be regulated by HST1 (FIG. 2B). There was no overlap between S1 and HST2, HST3, or HST4 regulated genes (FIG. 2D). Thus the majority of all transcriptional changes (88%) induced by S1 were mediated through SIR2 and a smaller subset (9%) through HST1 (FIG. 2B). These results indicate that S1 is a selective Sir2p inhibitor.

Sir2p is critical for silencing, yet the majority of the transcriptional changes induced by either chemical or genetic inactivation of the enzyme constituted transcriptional down-regulation (FIGS. 2, A and B). A number of these changes are known to be indirect. For instance, haploid specific genes are down-regulated by the gene products of the derepressed HMLα and HMRa loci (Marsh, L., et al. (1991) *Annu. Rev. Cell Biol.* 7, 699-728). S1, combined with the protein synthesis inhibitor cycloheximide, afforded an opportunity to identify genes that are directly regulated by Sir2p. Such an examination has not been possible before because conditional alleles of SIR2 are not available. The addition of cycloheximide did not affect the upregulation of genes by S1 treatment. In contrast, virtually all transcriptional down-regulation was abolished in the absence of new protein synthesis. This confirmed that the direct effect of Sir2p is to repress transcription (FIG. 2C). With the exception of a single gene, BPH1, the only genes that were up-regulated as a result of Sir2p inactivation in the presence of cycloheximide were subtelomeric genes and silent mating type loci, indicating that Sir2p activity does not affect transcription outside of these regions. Overall, these results are consistent with a recent study examining the location of Sir2p by genome-wide chromatin immunoprecipitation (Lieb, J. D., et al. (2001) *Nat. Genet.* 28, 327-34).

HDA Assay for Determination of Inhibition of Deacetylase Activity of Sir2p by S1.

Figure 3:
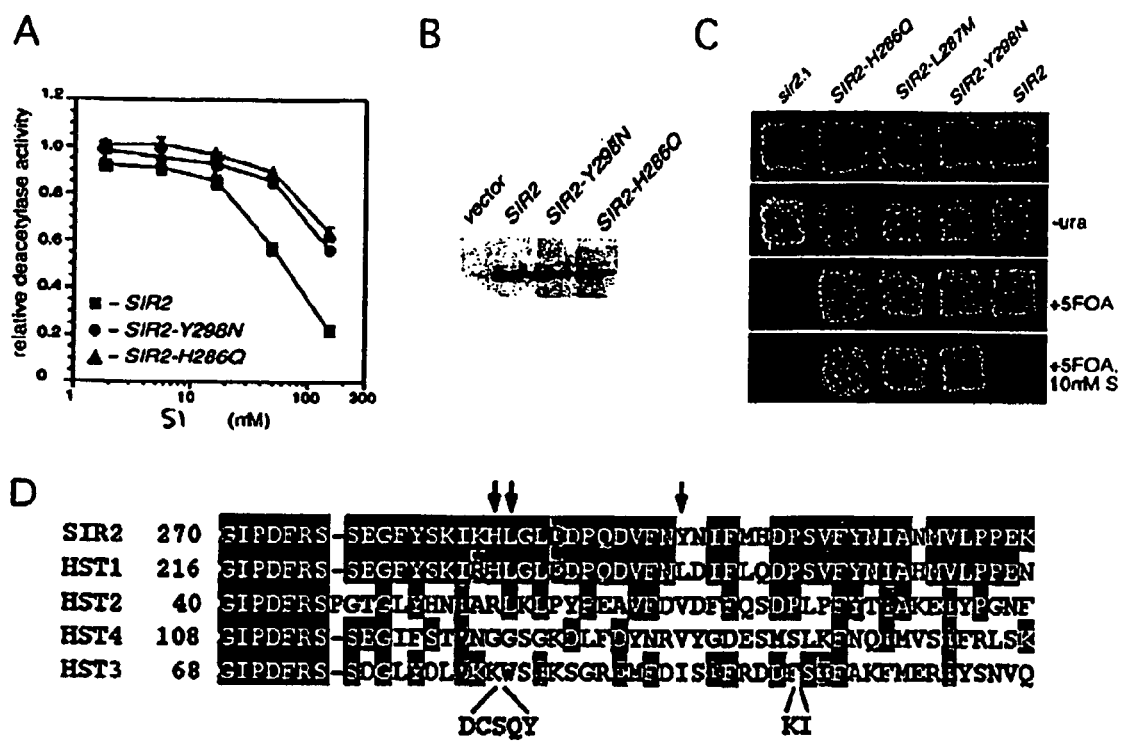
FIG. 3. (A) Inhibition of NAD-dependent histone deacetylase activity (HDA) of Sir2p by S1. (B) Imnmunoblot of Sir2p in whole cell lysates containing overexpressed wild type or drug resistant mutant SIR2. (C) Telomeric silencing in SIR2, sir2Δ and drug-resistant SIR2 mutants. (D) Sequence alignment between yeast Sir2p and Hst1-4p. The region displayed in the alignment contains the putative substrate-binding site. Arrows indicate the positions of residues that, when mutated in Sir2p, confer S1 resistance.

Without being bound to any particular theory, the phenotypic changes caused by S1 are thought to be the result of inhibition of the histone deacetylase activity of Sir2p. Accordingly, S1 was evaluated for its ability to inhibit the histone deacetylase activity of Sir2p in vitro. An [$^3$H]-acetylated histone H4 peptide was used in the assay which measured the NAD$^+$-dependent release of free [$^3$H]-acetate in the presence of whole yeast cell extract from an hst2 strain overexpressing yeast SIR2. A cell extract obtained from a SIR2 overexpressing hst2 strain had robust NAD$^+$-dependent histone deacetylase activity derived exclusively from Sir2p (FIGS. 3, A and B).

Briefly, histone H4 was chemically acetylated using the HDAC Assay Kit (Upstate Biotechnology). The whole cell extract is prepared as described (Smith, J. S. et al. (2000) *Proc. Natl. Acad. Sci. USA* 97, 6658-63) from an hst2Δ strain containing 2 µ plasmid with galactose-inducible wild type SIR2 (pAR14, Braunstein, M. et al. (1993) *Genes Dev.* 7, 592-604) or mutant SIR2 (GAL-SIR2-Y298N or GAL-SIR2-H286Q) or empty vector. For the histone deacetylase assays, 50 µg of yeast whole-cell protein extract was incubated with [$^3$H] acetylated histone H4-peptide (40,000 cpm) with or without 500 µM NAD$^+$ in a 100 µl reaction. The buffer contained 150 mM NaCl, 25 mM sodium phosphate pH 7.4 and 1 mM DTT. Reactions were incubated at 30° C. for 16 hours and were stopped by the addition of 25 µl of 1 N HCl and 0.15 N acetic acid. Released [$^3$H] acetate was extracted with 400 µl of ethyl acetate. S1 induced dose dependent inhibition of histone deacetylase activity in the yeast extract, with an IC50 of 60 µM (FIG. 3A). This result established Sir2p deacetylase activity as a direct target of S1.

Preparation and Identification of Mutations Conferring Drug Resistance to S1.

To obtain further insight into the molecular mechanism by which S1 inhibited deacetylase activity of Sir2p, mutant forms of Sir2p were generated that were resistant to the compound. The conserved core region of SIR2 was amplified using error prone PCR and was integrated into a SIR2 containing centromeric plasmid (pRS314-SIR2) by cotransformation into a sir2Δ strain with a URA3 telomeric marker (strain AB14053 MATα sir2 ppr1 adh4::URA3::TEL(VII-L)). Transformants from selective (-trp) media are pooled and aliquots plated onto selective media containing 5-fluoroorotic acid (5-FOA) and 10 µM S1. Plasmid DNA was recovered from the individual colonies and was retransformed into the test strain to assure that drug resistance was conferred by SIR2-containing plasmid. The entire SIR2 open reading frames from 20 independent plasmids conferring S1 resistance were sequenced. Mutations were introduced into a plasmid containing galactose inducible SIR2 (pAR14 (Braunstein, M. et al. (1993) *Genes Dev.* 7, 592-604)) using gap repair or site directed mutagenesis to make GAL-SIR2-Y298N and GAL-SIR2-H286Q. Three alleles of SIR2 (SIR2-H286Q, SIR2-L287Q and SIR2-Y298N) were identified that render yeast cells resistant to the anti-silencing effects of S1. Silencing was at normal levels in the drug resistant mutants in the absence of drug, but disruption of silencing in the mutants required higher concentrations of S1 than in wild type strains (FIG. 3C). In vitro, when compared to equivalent amounts of wild type Sir2p, mutant proteins exhibited similar histone deacetylase activity in the absence of drug, with increased resistance to the inhibitory effect of S1 (FIGS. 3, A and B).

The three mutations lie in close proximity within a region that is highly similar to human SIRT2. Most interestingly, the crystal structure of SIRT2 defines this region to be a hydrophobic cavity that is hypothesized to be the binding site for acetylated lysine peptides (Finnin, M. S., et al. (2001) *Nat. Struct. Biol.* 8, 621-5 and Min, J., et al. (2001) *Cell.* 105, 269-79.). As noted above, the expression profile of S1-treated cells had no overlap with mutant hst2, hst3, or hst4 strains, but did have some overlap with the hst1 profile. Of all the HST genes, Hst1p has the highest sequence similarity (86% identity) to Sir2p in the 50 amino acid region containing the S1 resistance mutations (FIG. 3D). Since Hst1p also acts to repress gene expression via hypoacetylation of histones (Rusche, L. N. & Rine, J. (2001) *Genes Dev.* 15, 955-67 and Sutton, A., et al. (2001) *Mol. Cell Biol.* 21, 3514-22.), it seems likely that this shared region defines a common binding pocket for acetylated histone tails in both proteins. Thus, it appears that S1 inhibits the deacetylase activity of Sir2p by blocking access to the acetylated histone binding pocket, or by altering the confirmation of the acetylated histone binding pocket, such that the deacetylase activity of Sir2p is inhibited.

Continuous Deacetylase Activity of Sir2p is Required for the Maintenance of the Silent State in Non-Dividing Cells.

The establishment of silencing in previously active chromatin is a cell cycle dependent event that can be accomplished only during S-phase (Li, Y. C., et al. (2001) Science 291, 650-3 and Kirchmaier, A. L. & Rine, J. (2001) Science 291, 646-50). Once established, the silent state needs to be maintained between cell divisions, after mitosis, in G1 and into the next S phase. Studies with a temperature sensitive allele of SIR3 demonstrated that silencing is quickly lost in G1-arrested cells after cells are shifted to the nonpermissive temperature (Miller, A. M. & Nasmyth, K. A. (1984) Nature 312, 247-51). In contrast, removal of the DNA silencer elements from the HMLα locus in G1-arrested cells does not disrupt silencing (Holmes, S. G. & Broach, J. R. (1996) Genes Dev. 10, 1021-32). The study with the temperature sensitive allele of SIR3 suggests that the presence of the entire SIR complex is required for the maintenance of a silent state.

Figure 4:
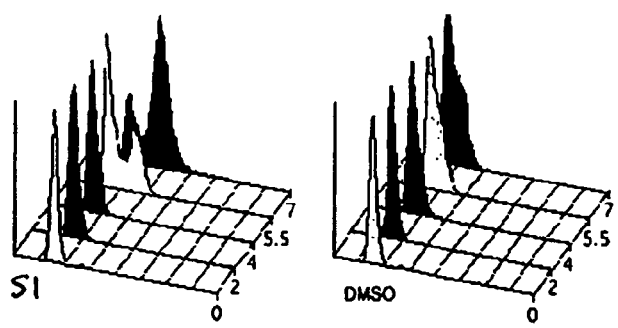
FIG. 4. (A) Cell cycle analysis of α factor arrested MATa cells treated with S1. (B) α2 mRNA expression from the silent HML locus in G1-arrested cells treated with S1. The RNA from MATα and MATa sir2Δ cells is included for comparison. The weak lower molecular weight band is due to cross hybridization to a2 mRNA.
Figure 4:
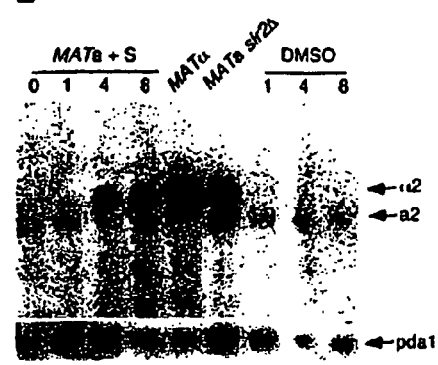

The requirement for the deacetylase activity of Sir2p for the maintenance of a silent state in non-dividing cells or whether Sir2p was dispensable once silent chromatin was formed was not established. To address this issue, the ability of S1 to inhibit the histone deacetylase activity of Sir2p was used. Briefly, MA Ta cells were first arrested in G1 using α factor and then treated with S1. While untreated cells remained arrested in G1, those treated with S1 progressed through the cell cycle (FIG. 4A). This was presumably due to loss of mating competence, a consequence of expression of the α2 gene from the "silent" HML locus. To test this idea more directly, a MATa strain with a single G1 cyclin gene (CLN3), which is under control of a galactose-inducible promoter (Cross, F. R. (1990) Mol. Cell Biol. 10, 6482-90), was arrested in G1 by replacing galactose with glucose in the media. Once the cells arrested in G1, they were treated with S1 or a DMSO control. While the cells remained arrested in G1 under both conditions, α2 mRNA expression from HML was detected only in the S1-treated cells (FIG. 4B). The lag period of several hours between the application of S1 and the appearance of α2 mRNA was similar to the delay before cell cycle progression was observed in the a factor arrested cells treated with S1 (described above). These results demonstrated that the deacetylase activity of Sir2p is continuously required for the maintenance of the silent state in non-dividing cells.

As a result of these studies, Sir2p must remain diligent in maintaining the silent state, in order to counteract the constant activity of histone acetylases. The acetylases may gain access to the chromatin in a targeted manner via transcriptional activators (Aparicio, O. M. & Gottschling, D. E. (1994) Genes Dev. 8, 1133-46 and Sekinger, E. A. & Gross, D. S. (2001) Cell 105, 403-14) or be part of a global histone acetylation maintenance system (Vogelauer, M., et al. (2000) Nature 408, 495-8). These results also support the idea that silent chromatin is not a static, rigid structure, but rather that it is in a dynamic equilibrium with silencing factor exchanging on and off the chromatin, even when cells are not dividing (Cheng, T. H. & Gartenberg, M. R. (2000) Genes Dev. 14, 452-63).

These results underscore the power of phenotypic screening in model systems to identify new compounds that are useful for dissecting complex biological processes such as silencing in vivo. To this end, the identification of an inhibitor of Sir2p complements the existing inhibitors of histone deacetylases (i.e. trapoxin and trichostatin (Taunton, J., et al. (1996) Science 272, 408-11)). In addition to histones, many other proteins are regulated by acetylation, including pRb, E2F and p53 proteins (Chan, H. M., et al. (2001) Nat. Cell Biol. 3, 667-74; Martinez-Balbas, M. A., et al. (2000) EMBO J. 19, 662-71; and Luo, J., et al. (2000) Nature 408, 377-81). Two recent reports (Vaziri, H., et al. (2001) Cell 107, 149-159 and Luo, J., et al. (2001) Cell 107, 137-148) implicate deacetylation of p53, by Sir2, in down-regulation of transcriptional and proapoptotic activities of p53 in response to DNA damage. Toxicity assays using S1 and a variety of DNA damaging agents have shown that S1 sensitizes mammalian cells to these agents, consistent with S1 abrogating Sir2p activity on p53. Thus, S1 is a useful component in the evaluation of Sir2p-like deacetylases as drug targets for treating cancer and other diseases (Wolffe, A. P. (2001) Oncogene 20, 2988-90 and Tycko, B. & Ashkenas, J. (2000) J. Clin. Invest 105, 245-6).

S1 Sensitization of Mammalian Cells to DNA Damage.

Figure 5:
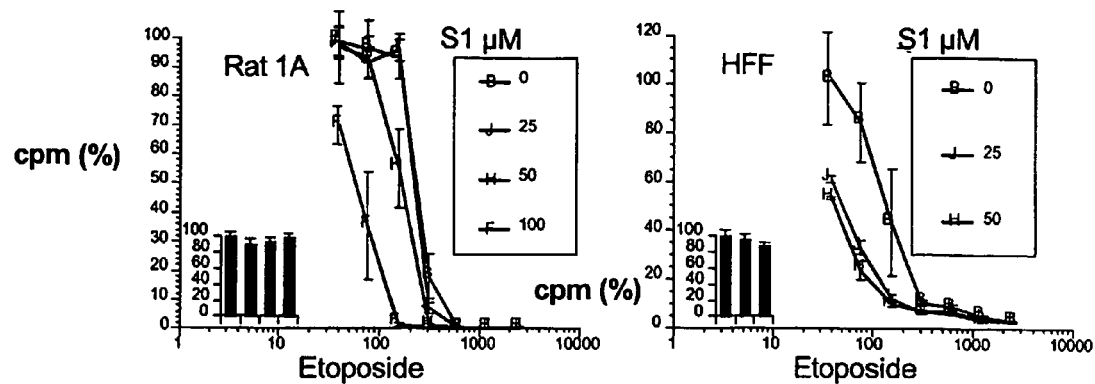
FIG. 5. S1 sensitizes mammalian cells to DNA damaging agents. The bar graph inset shows viability of cells treated with S1 relative to vehicle treated control.

To test whether S1 could sensitize cells to DNA damage, mammalian cells were exposed to etoposide, a DNA damaging agent, in the presence and absence of S1. Briefly, Rat1a and primary human fibroblasts (HFF) were treated with etoposide alone (0) or with S1 25, 50 and 100 µM) and etoposide for 72 hours. Viability of cells was assessed with 3H-thymidine incorporation. Viability of cells in etoposide relative to viability without etoposide is graphed for every concentration of S1. In both Rat1a cells and human foreskin fibroblast cells, S1 induced a dose-dependent sensitization to etoposide (FIG. 5).

FIG. 6 is a table of compounds useful in the present invention, and their activity as determined in the assays described above.

Although the foregoing invention has been described in some detail by way of illustration and example for purposes of clarity of understanding, it will be obvious that certain changes and modifications may be practiced within the scope of the appended claims. In addition, each reference provided herein is incorporated by reference in its entirety to the same extent as if each reference was individually incorporated by reference.

What is claimed is:

1. A method for treating lymphoma, comprising the step of administering to a subject in need thereof a therapeutically effective amount of a compound of Formula II:

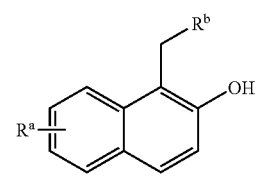

wherein
$R^a$ is a member selected from the group consisting of hydrogen, $C_{1-6}$alkyl, aryl, —$OR^e$, —$NR^eR^e$, —$CO_2R^e$, —$C(O)R^e$, —$C(O)NR^eR^e$, —CN, —$NO_2$ and halogen;
$R^b$ is:

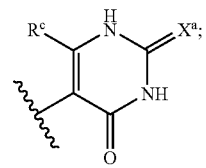

$X^a$ is a member selected from the group consisting of O, S and $NR^e$;

$R^c$ is a member selected from the group consisting of hydrogen, $C_{1-6}$alkyl and aryl optionally substituted with a member selected from the group consisting of hydrogen, $C_{1-6}$alkyl, aryl, $-OR^e$, $-NR^eR^e$, $-CN$, $-NO_2$ and halogen; and each instance of $R^e$ is independently a member selected from the group consisting of hydrogen and $C_{1-6}$alkyl.

2. The method of claim 1, wherein said method is for the treatment of a B-cell-derived non-Hodgkin lymphoma or a diffuse large B-cell lymphoma.

3. The method of claim 1, wherein said compound has the formula:

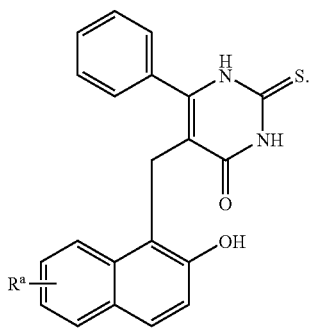

4. The method of claim 1, wherein said compound is administered with an antineoplastic agent.

5. The method of claim 4, wherein said antineoplastic agent is a member selected from the group consisting of antimetabolites, antifolates and other inhibitors of DNA synthesis, antisense oligonucleotides, biological response modifiers, DNA-alkylating agents, DNA intercalators, DNA repair agents, growth factor receptor kinase inhibitors, hormone agents, immunoconjugates, microtubule disruptors and topoisomerase I/II inhibitors.

6. A method of claim 5, wherein said antineoplastic agent is a member selected from the group consisting of cyclophosphamide, triethylenephosphoramide, triethylenethiophosphoramide, BCNU, bleomycin, busulfan, chlorambucil, cytarabine, dactinomycin, daunorubicin, docetaxol, doxorubicin, epirubicin, estramustine, dacarbazine, etoposide, fluorouracil, gemcitabine, ifosfamide, methotrexate, mitomycin, mitoxantrone, paclitaxel, procarbazine, temozolomide, teniposide, thioguanine, uracil mustard, vinblastine, vincristine, vinorelbine and vindesine.

7. The method of claim 6, wherein said antineoplastic agent is administered after said compound.

8. The method of claim 6, wherein said antineoplastic agent is administered simultaneously with said compound.

9. The method of claim 6, wherein said antineoplastic agent is administered prior to said compound.

10. The method of claim 1, wherein said lymphoma has metastasized.

\* \* \* \* \*

UNITED STATES PATENT AND TRADEMARK OFFICE
CERTIFICATE OF CORRECTION

PATENT NO. : 7,514,406 B2  Page 1 of 1
APPLICATION NO. : 10/496031
DATED : April 7, 2009
INVENTOR(S) : Antonio Bedalov, Daniel E. Gottschiling and Julian Simon It is certified that error appears in the above-identified patent and that said Letters Patent is hereby corrected as shown below:

Column 1, lines 20-21

"Institute Grant CA78746. The Government may have rights in certain aspects of this invention."

Should read

-- Institute Grant CA78746. The Government has certain rights in the invention. --

Signed and Sealed this

Twenty-ninth Day of December, 2009

David J. Kappos
*Director of the United States Patent and Trademark Office*

UNITED STATES PATENT AND TRADEMARK OFFICE
CERTIFICATE OF CORRECTION

PATENT NO. : 7,514,406 B2  Page 1 of 1
APPLICATION NO. : 10/496031
DATED : April 7, 2009
INVENTOR(S) : Antonio Bedalov, Daniel E. Gottschiling and Julian Simon It is certified that error appears in the above-identified patent and that said Letters Patent is hereby corrected as shown below:

Column 1, after line 21, please insert:

-- This invention was also supported by a Translational Research Program Award from the Leukemia & Lymphoma Society. --

Signed and Sealed this

Twentieth Day of April, 2010

David J. Kappos
*Director of the United States Patent and Trademark Office*

UNITED STATES PATENT AND TRADEMARK OFFICE
CERTIFICATE OF CORRECTION

PATENT NO. : 7,514,406 B2
APPLICATION NO. : 10/496031
DATED : April 7, 2009
INVENTOR(S) : Bedalov et al.

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by 427 days Delete the phrase "by 427 days" and insert -- by 991 days --

Signed and Sealed this

Twenty-second Day of June, 2010

David J. Kappos
*Director of the United States Patent and Trademark Office*